United States Patent
Shimizu et al.

(10) Patent No.: US 10,207,390 B2
(45) Date of Patent: Feb. 19, 2019

(54) PROCESSING END POINT DETECTION METHOD, POLISHING METHOD, AND POLISHING APPARATUS

(71) Applicants: EBARA CORPORATION, Tokyo (JP); Toshiba Memory Corporation, Tokyo (JP)

(72) Inventors: Noburu Shimizu, Tokyo (JP); Shinro Ohta, Tokyo (JP); Koji Maruyama, Tokyo (JP); Yoichi Kobayashi, Tokyo (JP); Ryuichiro Mitani, Tokyo (JP); Shunsuke Nakai, Tokyo (JP); Atsushi Shigeta, Tokyo (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 1405 days.

(21) Appl. No.: 14/017,620

(22) Filed: Sep. 4, 2013

(65) Prior Publication Data

US 2014/0004773 A1 Jan. 2, 2014

Related U.S. Application Data

(62) Division of application No. 12/311,560, filed as application No. PCT/JP2007/070030 on Oct. 5, 2007, now Pat. No. 8,554,356.

(30) Foreign Application Priority Data

Oct. 6, 2006 (JP) ................................. 2006-274622
Dec. 7, 2006 (JP) ................................. 2006-330383

(51) Int. Cl.
 B24B 49/04 (2006.01)
 B24B 37/013 (2012.01)
(Continued)

(52) U.S. Cl.
 CPC ............ *B24B 49/04* (2013.01); *B24B 37/013* (2013.01); *B24B 49/12* (2013.01); *B24D 7/12* (2013.01);
(Continued)

(58) Field of Classification Search
 CPC ....... B24B 49/04; B24B 37/013; B24B 49/12; B24B 49/16; G05B 19/406;
(Continued)

(56) References Cited

U.S. PATENT DOCUMENTS 5,644,503 A 7/1997 Ito et al.
5,658,183 A * 8/1997 Sandhu ............... B23Q 15/013
 250/559.27
(Continued)

FOREIGN PATENT DOCUMENTS

JP 11-33901 2/1999
JP 2000-33561 2/2000
(Continued)

OTHER PUBLICATIONS

International Search Report dated Feb. 12, 2008 for International Application No. PCT/JP2007/070030.

*Primary Examiner* — Mohammad Ali
*Assistant Examiner* — Kelvin Booker
(74) *Attorney, Agent, or Firm* — Wenderoth, Lind & Ponack, L.L.P.

(57) ABSTRACT

A processing end point detection method detects a timing of a processing end point (e.g., polishing stop, changing of polishing conditions) by calculating a characteristic value of a surface of a workpiece (an object of polishing) such as a substrate. This method includes producing a spectral waveform indicating a relationship between reflection intensities and wavelengths at a processing end point, with use of a reference workpiece or simulation calculation, based on the (Continued)

spectral waveform, selecting wavelengths of a local maximum value and a local minimum value of the reflection intensities, calculating the characteristic value with respect to a surface, to be processed, from reflection intensities at the selected wavelengths, setting a distinctive point of time variation of the characteristic value at a processing end point of the workpiece as the processing end point, and detecting the processing end point of the workpiece by detecting the distinctive point during processing of the workpiece.

12 Claims, 18 Drawing Sheets

(51) Int. Cl.
| | |
|---|---|
| B24D 7/12 | (2006.01) |
| G01N 21/55 | (2014.01) |
| G05B 19/40 | (2006.01) |
| B24B 49/12 | (2006.01) |
| G01N 21/95 | (2006.01) |
| H01L 21/66 | (2006.01) |
| G05B 19/406 | (2006.01) |
| B24B 49/16 | (2006.01) |
| G01B 11/06 | (2006.01) |
| G05B 19/4065 | (2006.01) |

(52) U.S. Cl.
CPC ......... *G01N 21/55* (2013.01); *G01N 21/9501* (2013.01); *G05B 19/406* (2013.01); *H01L 22/26* (2013.01); *B24B 49/16* (2013.01); *G01B 11/0675* (2013.01); *G05B 19/4065* (2013.01); *H01L 2924/0002* (2013.01)

(58) Field of Classification Search
CPC .......... G05B 19/4065; G01N 21/9501; G01N 21/55; H01L 22/26; H01L 2924/0002; B24D 7/12; G01B 11/0675
See application file for complete search history.

(56) References Cited

U.S. PATENT DOCUMENTS

| | | | |
|---|---|---|---|
| 5,700,180 A * | 12/1997 | Sandhu | B23Q 15/013 451/21 |
| 5,807,761 A | 9/1998 | Coronel et al. | |
| 5,989,928 A | 11/1999 | Nakata et al. | |
| 6,068,539 A * | 5/2000 | Bajaj | B24B 21/04 451/41 |
| 6,077,783 A * | 6/2000 | Allman | B24B 37/042 257/E21.304 |
| 6,108,091 A * | 8/2000 | Pecen | B24B 37/205 356/369 |
| 6,117,779 A * | 9/2000 | Shelton | B24B 37/04 257/E21.244 |
| 6,146,248 A * | 11/2000 | Jairath | B24B 21/04 257/E21.528 |
| 6,172,756 B1 | 1/2001 | Chalmers et al. | |
| 6,204,922 B1 | 3/2001 | Chalmers | |
| 6,241,847 B1 * | 6/2001 | Allman | B24B 37/013 257/E21.304 |
| 6,248,000 B1 * | 6/2001 | Aiyer | B24B 37/013 451/41 |
| 6,271,047 B1 | 8/2001 | Ushio et al. | |
| 6,273,792 B1 * | 8/2001 | Meloni | B24B 37/0053 451/287 |
| 6,306,009 B1 * | 10/2001 | Sandhu | B23Q 15/013 451/288 |
| 6,354,922 B1 * | 3/2002 | Sakurai | B24B 37/042 257/E21.23 |
| 6,358,128 B1 * | 3/2002 | Sakurai | B24B 37/042 257/E21.23 |
| 6,383,332 B1 | 5/2002 | Shelton et al. | |
| 6,393,368 B1 | 5/2002 | Ito et al. | |
| 6,413,147 B1 * | 7/2002 | Litvak | B24B 37/013 451/10 |
| 6,416,615 B1 * | 7/2002 | Lai | B24B 37/0053 156/345.13 |
| 6,476,921 B1 * | 11/2002 | Saka | B24B 37/013 356/630 |
| 6,489,624 B1 | 12/2002 | Ushio et al. | |
| 6,491,569 B2 | 12/2002 | Bibby et al. | |
| 6,514,121 B1 * | 2/2003 | Halley | B24B 9/065 451/269 |
| 6,517,419 B1 * | 2/2003 | Halley | B24B 9/065 451/443 |
| 6,520,843 B1 * | 2/2003 | Halley | B24B 9/065 451/285 |
| 6,628,397 B1 * | 9/2003 | Nikoonahad | B24B 37/005 356/445 |
| 6,629,874 B1 * | 10/2003 | Halley | B24B 9/065 451/11 |
| 6,630,995 B1 | 10/2003 | Hunter | |
| 6,635,573 B2 | 10/2003 | Pau et al. | |
| 6,654,132 B1 * | 11/2003 | Schietinger | B24B 37/013 356/237.2 |
| 6,670,200 B2 | 12/2003 | Ushio et al. | |
| 6,671,051 B1 * | 12/2003 | Nikoonahad | B24B 37/005 356/445 |
| 6,676,482 B2 | 1/2004 | Bibby et al. | |
| 6,679,756 B2 | 1/2004 | Ishikawa et al. | |
| 6,776,692 B1 * | 8/2004 | Zuniga | B24B 37/013 451/11 |
| 6,809,809 B2 | 10/2004 | Kinney et al. | |
| 6,821,794 B2 | 11/2004 | Laursen et al. | |
| 6,934,638 B2 | 8/2005 | Ito et al. | |
| 6,950,193 B1 * | 9/2005 | Discenzo | G01B 11/06 356/482 |
| 6,963,407 B2 | 11/2005 | Abe et al. | |
| 6,972,848 B2 | 12/2005 | Usui et al. | |
| 6,976,901 B1 * | 12/2005 | Halley | B24B 37/04 451/285 |
| 6,991,514 B1 * | 1/2006 | Meloni | B24B 49/12 451/288 |
| 6,991,516 B1 * | 1/2006 | David | B24B 37/04 451/41 |
| 7,024,268 B1 * | 4/2006 | Bennett | G05B 19/41875 438/692 |
| 7,025,658 B2 | 4/2006 | David | |
| 7,052,920 B2 | 5/2006 | Ushio et al. | |
| 7,074,110 B1 * | 7/2006 | Wolf | B24B 37/005 451/288 |
| 7,097,537 B1 * | 8/2006 | David | B24B 49/105 451/10 |
| 7,110,886 B2 | 9/2006 | Ito et al. | |
| 7,153,185 B1 * | 12/2006 | Birang | B24B 37/005 451/10 |
| 7,252,575 B2 | 8/2007 | Kobayashi et al. | |
| 7,259,866 B2 | 8/2007 | Usui et al. | |
| 7,356,446 B2 | 4/2008 | Ito et al. | |
| 7,438,627 B2 | 10/2008 | Kobayashi et al. | |
| 7,500,901 B2 * | 3/2009 | Swedek | B24B 49/10 451/41 |
| 7,565,084 B1 * | 7/2009 | Wach | H04J 14/04 398/183 |
| 7,645,181 B2 | 1/2010 | Kobayashi et al. | |
| 7,728,967 B2 | 6/2010 | Ochiai et al. | |
| 7,892,069 B2 | 2/2011 | Na et al. | |
| 7,952,708 B2 | 5/2011 | Ravid et al. | |
| 8,014,962 B2 | 9/2011 | Ito et al. | |
| 8,094,297 B2 | 1/2012 | Ochiai et al. | |
| 8,110,814 B2 | 2/2012 | Ward et al. | |
| 8,115,936 B2 | 2/2012 | Ochiai et al. | |
| 8,157,616 B2 | 4/2012 | Shimizu et al. | |
| 8,337,277 B2 | 12/2012 | Shiro et al. | |
| 8,342,907 B2 | 1/2013 | Kobayashi et al. | |
| 8,388,408 B2 | 3/2013 | Kobayashi et al. | |
| 2001/0006870 A1 * | 7/2001 | Moore | B24B 49/006 451/5 |

(56) References Cited

U.S. PATENT DOCUMENTS

| | | |
|---|---|---|
| 2001/0039064 A1 | 11/2001 | Ushio et al. |
| 2002/0001862 A1 | 1/2002 | Ushio et al. |
| 2002/0013007 A1 | 1/2002 | Hasegawa et al. |
| 2002/0023715 A1* | 2/2002 | Kimura ............... B24B 37/042 156/345.12 |
| 2002/0055192 A1* | 5/2002 | Redeker ............... B24B 37/013 438/8 |
| 2002/0077031 A1* | 6/2002 | Johansson ............ B24B 37/013 451/6 |
| 2002/0127951 A1* | 9/2002 | Ishikawa ............... B24B 37/013 451/6 |
| 2002/0147550 A1 | 10/2002 | Ito et al. |
| 2002/0155788 A1 | 10/2002 | Bibby et al. |
| 2002/0164925 A1* | 11/2002 | Swedek ............... B24B 37/013 451/5 |
| 2003/0045100 A1* | 3/2003 | Saka ............... B24B 37/013 438/689 |
| 2003/0082919 A1 | 5/2003 | Pau et al. |
| 2003/0087459 A1 | 5/2003 | Laursen et al. |
| 2003/0109198 A1* | 6/2003 | Lee ............... B23H 5/08 451/8 |
| 2003/0205664 A1 | 11/2003 | Abe et al. |
| 2004/0012775 A1 | 1/2004 | Kinney et al. |
| 2004/0080050 A1 | 4/2004 | McMillin et al. |
| 2004/0176014 A1* | 9/2004 | Bennett ............... B24B 37/013 451/5 |
| 2004/0259472 A1* | 12/2004 | Chalmers ............ B24B 37/013 451/5 |
| 2005/0023149 A1* | 2/2005 | Nakada ............... C25D 17/06 205/137 |
| 2005/0051437 A1* | 3/2005 | Kurashina ........... H01L 21/2885 205/143 |
| 2005/0061659 A1* | 3/2005 | Kurashina ............ C25D 5/06 204/198 |
| 2005/0066739 A1* | 3/2005 | Gotkis ............... B24B 37/015 73/760 |
| 2005/0105103 A1* | 5/2005 | Schietinger ........... B24B 37/013 356/630 |
| 2005/0173259 A1* | 8/2005 | Mavliev ............... B23H 5/08 205/645 |
| 2005/0251349 A1 | 11/2005 | Ito et al. |
| 2006/0040586 A1* | 2/2006 | Arai ............... B24B 37/042 451/5 |
| 2006/0141907 A1* | 6/2006 | Rudolph ............... B24B 37/013 451/6 |
| 2006/0166606 A1* | 7/2006 | Kobayashi ........... B24B 49/12 451/6 |
| 2006/0166608 A1* | 7/2006 | Chalmers ............ B24B 37/013 451/6 |
| 2006/0271310 A1 | 11/2006 | Ito et al. |
| 2007/0157730 A1 | 7/2007 | Ochiai et al. |
| 2007/0205112 A1* | 9/2007 | Kodera ............... B23H 5/08 205/641 |
| 2007/0243795 A1* | 10/2007 | Kobayashi ........... B24B 37/005 451/5 |
| 2007/0243797 A1* | 10/2007 | Fukunaga ............ B24B 37/042 451/8 |
| 2007/0251922 A1* | 11/2007 | Swedek ............... B24B 37/013 216/84 |
| 2007/0254557 A1 | 11/2007 | Kobayashi et al. |
| 2007/0254558 A1* | 11/2007 | Kodera ............... B24B 37/005 451/28 |
| 2008/0172186 A1 | 7/2008 | Ito et al. |
| 2008/0188162 A1* | 8/2008 | Kobata ............... B23H 5/08 451/8 |
| 2008/0242197 A1* | 10/2008 | Fujita ............... B24B 49/10 451/8 |
| 2009/0011680 A1 | 1/2009 | Kobayashi et al. |
| 2009/0023361 A1* | 1/2009 | Matsuzaki ........... B24B 49/105 451/5 |
| 2009/0036024 A1* | 2/2009 | Matsuzaki ........... B24B 37/013 451/5 |
| 2009/0042480 A1 | 2/2009 | Shiro et al. |
| 2009/0137190 A1* | 5/2009 | Togawa ............... B24B 37/013 451/8 |
| 2009/0191791 A1 | 7/2009 | Fukushima et al. |
| 2009/0298387 A1 | 12/2009 | Shimizu et al. |
| 2010/0029177 A1* | 2/2010 | Kobayashi ........... B24B 37/04 451/5 |
| 2010/0075576 A1 | 3/2010 | Kobayashi et al. |
| 2010/0093260 A1 | 4/2010 | Kobayashi et al. |
| 2010/0199768 A1 | 8/2010 | Ochiai et al. |
| 2010/0199769 A1 | 8/2010 | Ochiai et al. |
| 2010/0208248 A1 | 8/2010 | Ochiai et al. |
| 2011/0287694 A1 | 11/2011 | Benvegnu et al. |
| 2012/0048021 A1 | 3/2012 | Ochiai et al. |
| 2013/0149938 A1 | 6/2013 | Kobayashi et al. |

FOREIGN PATENT DOCUMENTS

| | | |
|---|---|---|
| JP | 2004-514273 | 5/2004 |
| JP | 2004-154928 | 6/2004 |
| KR | 2001-0102277 | 11/2001 |
| WO | 2002/10729 | 2/2002 |
| WO | 2005/123335 | 12/2005 |

\* cited by examiner

SENSOR PATHS ON WAFER
(TT/TR=70/71min−1)

SIGNAL WAVEFORM
(TT/TR=70/71 min−1, MOVING AVERAGE TIME 5 SECONDS)

SIGNAL WAVEFORM
(TT/TR=70/77 min−1, MOVING AVERAGE TIME 5 SECONDS)

FIG. 27

| n/m | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | 1.000 | 0.500 | 0.333 | 0.250 | 0.200 | 0.167 | 0.143 | 0.125 | 0.111 | 0.100 | 0.091 | 0.083 | 0.077 | 0.071 | 0.067 | 0.063 |
| 2 | 2.000 | NA | 0.667 | NA | 0.400 | NA | 0.286 | NA | 0.222 | NA | 0.182 | NA | 0.154 | NA | 0.133 | NA |
| 3 | 3.000 | 1.500 | NA | 0.750 | 0.600 | NA | 0.429 | 0.375 | NA | 0.300 | 0.273 | NA | 0.231 | 0.214 | NA | 0.188 |
| 4 | 4.000 | NA | 1.333 | NA | 0.800 | NA | 0.571 | NA | 0.444 | NA | 0.364 | NA | 0.308 | NA | 0.267 | NA |
| 5 | 5.000 | 2.500 | 1.667 | 1.250 | NA | 0.833 | 0.714 | 0.625 | 0.556 | NA | 0.455 | 0.417 | 0.385 | 0.357 | NA | 0.313 |
| 6 | 6.000 | NA | NA | NA | 1.200 | NA | 0.857 | NA | NA | NA | 0.545 | NA | 0.462 | NA | 0.467 | NA |
| 7 | 7.000 | 3.500 | 2.333 | 1.750 | 1.400 | 1.167 | NA | 0.875 | 0.778 | 0.700 | 0.636 | 0.583 | 0.538 | NA | 0.467 | 0.438 |
| 8 | 8.000 | NA | 2.667 | NA | 1.600 | NA | 1.143 | NA | 0.889 | NA | 0.727 | NA | 0.615 | NA | 0.533 | NA |
| 9 | 9.000 | 4.500 | NA | 2.250 | 1.800 | 1.500 | 1.286 | 1.125 | NA | 0.900 | 0.818 | NA | 0.692 | 0.643 | NA | 0.563 |
| 10 | 10.000 | NA | 3.333 | NA | NA | NA | 1.429 | NA | 1.111 | NA | 0.909 | NA | 0.769 | NA | 0.733 | NA |
| 11 | 11.000 | 5.500 | 3.667 | 2.750 | 2.200 | 1.833 | 1.571 | 1.375 | 1.222 | 1.100 | NA | 0.917 | 0.846 | 0.786 | NA | 0.688 |
| 12 | 12.000 | NA | NA | NA | 2.400 | NA | 1.714 | NA | 1.333 | NA | 1.091 | NA | 0.923 | NA | 0.867 | NA |
| 13 | 13.000 | 6.500 | 4.333 | 3.250 | 2.600 | 2.167 | 1.857 | 1.625 | 1.444 | 1.300 | 1.182 | 1.083 | NA | 0.929 | NA | 0.813 |
| 14 | 14.000 | NA | 4.667 | NA | 2.800 | NA | NA | NA | 1.556 | NA | 1.273 | NA | 1.077 | NA | 0.933 | NA |
| 15 | 15.000 | 7.500 | NA | 3.750 | 3.000 | NA | 2.143 | 1.875 | 1.667 | 1.500 | 1.364 | NA | 1.154 | 1.071 | NA | 0.938 |
| 16 | 16.000 | NA | 5.333 | NA | 3.200 | NA | 2.286 | NA | 1.778 | NA | 1.455 | NA | 1.231 | NA | 1.067 | NA |
| 17 | 17.000 | 8.500 | 5.667 | 4.250 | 3.400 | 2.833 | 2.429 | 2.125 | 1.889 | 1.700 | 1.545 | 1.417 | 1.308 | 1.214 | 1.133 | 1.063 |
| 18 | 18.000 | NA | NA | NA | 3.600 | NA | 2.571 | NA | NA | NA | 1.636 | NA | 1.385 | NA | NA | NA |
| 19 | 19.000 | 9.500 | 6.333 | 4.750 | 3.800 | 3.167 | 2.714 | 2.375 | 2.111 | 1.900 | 1.727 | 1.583 | 1.462 | 1.357 | 1.267 | 1.188 |
| 20 | 20.000 | NA | 6.667 | NA | NA | NA | 2.857 | NA | 2.222 | NA | 1.818 | NA | 1.538 | NA | NA | NA |

PROCESSING END POINT DETECTION METHOD, POLISHING METHOD, AND POLISHING APPARATUS

TECHNICAL FIELD

The present invention relates to a processing end point detection method for detecting a timing of a processing end point (e.g., polishing stop, changing of polishing conditions, etching stop, film-formation stop, and the like) by calculating a characteristic value of a surface of a workpiece (an object of polishing) such as a substrate.

The present invention also relates to a polishing method and polishing apparatus for polishing a substrate, such as a semiconductor wafer, to planarize the substrate.

BACKGROUND ART

The trend of recent years in a semiconductor device has been a highly integrated structure, which requires fine interconnects and multi-layered structure. To realize the fine interconnects and the multi-layered structure, it is necessary to planarize a surface of a substrate. Chemical mechanical polishing (CMP) is conventionally used to remove irregularities from the surface of the substrate to thereby planarize the surface.

In the chemical mechanical polishing process, polishing operation has to be stopped at a desired point after the substrate has been polished for a predetermined period of time. For example, it may be desirable to leave an insulating layer, such as $SiO_2$, (such an insulating layer is referred to as an interlevel film because a layer, e.g., a metal layer, is further formed on the insulating layer in a subsequent process) on metal interconnects of Cu or Al. In this case, if the substrate is polished more than required, a surface of a lower-level metal film is exposed. Therefore, the polishing process needs to be finished so as to leave the interlevel film with a predetermined thickness.

In the fabrication process of the semiconductor device, a predetermined pattern of interconnect trenches is formed on a surface of a substrate, and the interconnect trenches are filled up with Cu (copper) or its alloy. Then, unwanted portions of Cu or its alloy are removed from the surface of the substrate by the chemical mechanical polishing (CMP). When the Cu layer is polished by the CMP process, it is necessary to selectively remove the Cu layer from the substrate so as to leave only the Cu layer in the interconnect trenches. Specifically, it is necessary to remove the Cu layer in areas other than the interconnect trenches until the insulating film (which is made from $SiO_2$ or the like) is exposed.

In this case, if the Cu layer in the interconnect trenches is excessively polished off together with the insulating film, a circuit resistance can increase and the entire substrate has to be discarded, resulting in a large loss. On the other hand, if the Cu layer is polished insufficiently and remains on the insulating film, circuits are not separated well and short-circuit occurs. As a result, polishing of the Cu layer should be performed again, resulting in an increased manufacturing cost.

There has been known a polishing state monitoring apparatus for measuring an intensity of a reflected light using an optical sensor and detecting an end point of the CMP process based on the measured intensity of the reflected light. This polishing state monitoring apparatus includes the optical sensor having a light-emitting element and a light-detecting element. Light is applied from the optical sensor to a surface of a substrate during polishing of the surface. An end point of the CMP process is determined from a change in reflection intensity of the light from the surface of the substrate.

The following methods are known for measuring optical characteristics in the above-mentioned CMP process.

(1) Light from a monochromatic light source, such as a semiconductor laser or a light-emitting diode (LED), is applied to the surface, being polished, of the substrate and a change in the intensity of reflected light is detected.

(2) White light is applied to the surface of the substrate, and a spectral (ratio) reflection intensity is compared with a pre-stored spectral (ratio) reflection intensity for a polishing end point.

There has recently been developed a polishing state monitoring apparatus constructed to estimate an initial film thickness of a substrate, apply a laser beam to the substrate, and approximate a time variation of measurements of the intensity of reflected light from the substrate with a sine-wave model function to thereby calculate a film thickness.

There has also been proposed a method of detecting a polishing end point based on a time variation of a characteristic value of a substrate. This characteristic value is calculated by multiplying spectral data, obtained by applying light to the substrate, by a weight function and integrating the resultant spectral data (for example, see Japanese laid-open patent publication No. 2004-154928).

However, in the above-described conventional methods, it is difficult to detect a distinctive point (i.e., a point of distinctive change in the reflection intensity or the characteristic value) which serves as an index indicating a polishing end point. This makes it difficult to detect an accurate polishing end point. For example, when using a monochromatic light source, a relationship between a film thickness and a signal of the reflection intensity is determined uniquely according to a wavelength of the light source. In this case, the distinctive point may not always appear when a target film thickness, i.e., a polishing end point, is reached. Moreover, it is difficult to correct the manner of appearance.

On the other hand, when using a multiwavelength light such as white light, it is possible to select a desired wavelength so that a distinctive point of the reflection intensity appears when a desired film thickness is reached. However, selection of an optimum wavelength for a structure of a workpiece entails trial and error. As a result, a lot of time is needed for the selection process. Moreover, it is difficult to verify whether the wavelength selected is best suited.

A polishing apparatus having a top ring with multiple chambers therein is known as an apparatus for performing the above-mentioned CMP. This type of polishing apparatus is capable of adjusting pressures in the chambers independently. In this polishing apparatus, a sensor is provided so as to measure a physical quantity associated with a thickness of a film on a substrate and a monitoring signal is produced based on this physical quantity. Prior to polishing of the substrate, a reference signal that indicates a relationship between the monitoring signal and times is prepared in advance. During polishing of the substrate, pressing forces of the top ring are adjusted such that monitoring signals, obtained at plural measuring points on the substrate, converge on the reference signal, whereby a uniform film thickness can be realized over the surface of the substrate (for example, see WO 2005/123335).

A highly-functional CPU has recently been developed with the trend of a high-speed and highly-integrated semiconductor device. This highly-functional CPU incorporates therein several functions including a memory section and a calculating section in a single semiconductor chip. In this semiconductor chip, areas with different pattern densities and different structures coexist. Moreover, a chip size has becoming larger year by year, and some types of CCD devices have a film size of 24×36 mm. In semiconductor fabrications, a lot of chips are formed on a single substrate. Therefore, areas with different pattern densities and different structures coexist in a surface of the substrate. Further, for the purpose of evaluating a finished device, a substrate may have an electrical characteristic evaluation pattern that is greatly different from device patterns.

When polishing such a substrate, a change in thickness of a film on a surface of the substrate is monitored by applying light to the surface of the substrate and detecting the reflected light from the substrate by an optical sensor. However, the intensity of the reflected light from the surface of the substrate varies intricately depending not only on the change in film thickness as a result of polishing, but also on the patterns and structures of the devices. Specifically, since a polishing table and a top ring are rotating during polishing, the optical sensor, which is provided in the polishing table, passes through different areas with different pattern densities and different structures every time the sensor scans the surface of the substrate. Consequently, the intensity of the reflected light can vary due to the influence of the device patterns and structures. This varying reflection intensity is superimposed as a noise on a signal indicating a change in the film thickness. In such a case, even if smoothing of the signal is performed, the change in film thickness cannot be accurately monitored because the noise is large. This affects an accuracy of polishing end point detection and a polishing control for a uniform film thickness.

In a case where an object of polishing is a copper film, an eddy current sensor is often used to measure a film thickness. Typically, the copper film is formed by plating. A plating apparatus for performing copper plating generally has cathode electrodes arranged at equal intervals along a periphery of a substrate. A plating solution is supplied to a surface of the substrate, with the plating solution being retained by a seal member. In this state, a voltage is applied between the cathode electrodes and an anode electrode in the plating solution to thereby plate the surface of the substrate with copper. Use of such a plating apparatus can present a problem of variations in film thickness along the periphery of the substrate because of variations in contact resistance of the cathode electrodes or because of sealing performance of the seal member. As a result, the sensor may scan only thick portions or thin portions of the film depending on times during polishing, thus failing to measure an average film thickness.

DISCLOSURE OF INVENTION

The present invention has been made in view of the above drawbacks. It is therefore a first object of the present invention to provide a processing end point detection method and a processing apparatus capable of easily obtaining a characteristic value that has a distinctive point, such as a local maximal value or a local minimal value, at a target film thickness to realize an accurate processing end point detection.

It is a second object of the present invention to provide a polishing method and a polishing apparatus capable of reducing an influence of various areas with different pattern densities and different structures or variations in film thickness along a circumferential direction produced in a film formation process on an output signal of a sensor to realize an accurate polishing end point detection and a uniform film thickness.

In order to achieve the first object, the present invention provides a processing end point detection method for detecting a processing end point based on a characteristic value with respect to a surface of a workpiece, the characteristic value being calculated using a spectral waveform of reflected light obtained by applying light to the surface of the workpiece. The method includes: producing a spectral waveform indicating a relationship between reflection intensities and wavelengths at a processing end point, with use of a reference workpiece or simulation calculation; based on the spectral waveform, selecting wavelengths of a local maximum value and a local minimum value of the reflection intensities; calculating the characteristic value with respect to a surface, to be processed, from reflection intensities at the selected wavelengths; setting a distinctive point of time variation of the characteristic value at a processing end point of a workpiece as the processing end point; and detecting the processing end point of the workpiece by detecting the distinctive point during processing of the workpiece.

Examples of the processing of the workpiece include polishing of a substrate having a film thereon and forming a film on a substrate.

In a preferred aspect of the present invention, the method further includes averaging the reflection intensities at each wavelength over a processing time of the reference workpiece to determine an average reflection intensity at each wavelength; and producing a reference spectral waveform by dividing each of the reflection intensities, obtained at the processing end point of the reference workpiece, by the corresponding average reflection intensity. The selecting of the wavelengths of the local maximum value and the local minimum value is performed based on the reference spectral waveform.

In a preferred aspect of the present invention, the method further includes defining a weight function having a weight centered on the selected wavelength of the local maximum value, wherein the calculating of the characteristic value comprises determining the characteristic value with respect to the surface of the workpiece by multiplying the reflection intensities, obtained by application of the light to the surface of the workpiece, by the weight function and integrating the resultant reflection intensities, and the detecting of the processing end point comprises detecting the processing end point of the workpiece by detecting a distinctive point of time variation of the characteristic value.

In a preferred aspect of the present invention, the method further includes shifting the selected wavelengths to shorter or longer wavelengths.

Another aspect of the present invention provides a processing end point detection method of detecting a processing end point based on a characteristic value with respect to a surface of a workpiece, the characteristic value being calculated using a spectral waveform of reflected light obtained by applying multiwavelength light to the surface of the workpiece. The method includes averaging reflection intensities at each wavelength over a processing time to determine an average reflection intensity at each wavelength, with use of a reference workpiece or simulation calculation; producing a reference spectral waveform by dividing each of reflection intensities, obtained by application of the multiwavelength light to the surface of the workpiece during processing thereof, by the corresponding average reflection intensity; and detecting a processing end point of the workpiece by monitoring the reference spectral waveform.

Another aspect of the present invention provides a processing apparatus including: a light source configured to apply light to a surface of a workpiece; a light-receiving unit configured to receive reflected light from the surface of the workpiece; a spectroscope unit configured to divide the reflected light received by the light-receiving unit into a plurality of light rays and convert the light rays into electrical information; and a processor configured to process the electrical information from the spectroscope unit. The processor is configured to average reflection intensities at each wavelength over a processing time of a reference workpiece to determine an average reflection intensity at each wavelength, produce a reference spectral waveform by dividing each of the reflection intensities, obtained at the processing end point of the reference workpiece, by the corresponding average reflection intensity, select wavelengths of a local maximum value and a local minimum value of the reference spectral waveform, calculating the characteristic value with respect to a surface of the reference workpiece from reflection intensities at the selected wavelengths, set a distinctive point of time variation of the characteristic value at a processing end point of a workpiece as a processing end point, and detect the processing end point of the workpiece by detecting the distinctive point during processing of the workpiece.

Another aspect of the present invention provides a processing apparatus including: a light source configured to apply multiwavelength light to a surface of a workpiece; a light-receiving unit configured to receive reflected light from the surface of the workpiece; a spectroscope unit configured to divide the reflected light received by the light-receiving unit into a plurality of light rays and convert the light rays into electrical information; and a processor configured to process the electrical information from the spectroscope unit. The processor is configured to average reflection intensities at each wavelength over a processing time of a reference workpiece to determine an average reflection intensity at each wavelength, produce a reference spectral waveform by dividing each of reflection intensities, obtained by application of the multiwavelength light to the surface of the workpiece during processing thereof, by the corresponding average reflection intensity, and detect a processing end point of the workpiece by monitoring the reference spectral waveform.

According to the present invention as described above, it is possible to obtain the characteristic value which has a distinctive changing point at the polishing end point and has a good signal-to-noise ratio depending on a device pattern of a substrate. Therefore, an accurate polishing end point can be detected.

In order to achieve the second object, the present invention provides a polishing method including: holding and rotating a workpiece by a top ring; pressing the workpiece against a polishing surface on a rotating polishing table to polish the workpiece; and monitoring a surface state of the workpiece with a sensor provided on the polishing table during polishing of the workpiece. A rotational speed of the top ring and a rotational speed of the polishing table are set such that paths of the sensor, described on a surface of the workpiece in a predetermined measuring time, are distributed substantially evenly over an entire circumference of the surface of the workpiece.

In a preferred aspect of the present invention, the rotational speed of the top ring and the rotational speed of the polishing table are set such that a path of the sensor rotates about 0.5×N times on the surface of the workpiece in the predetermined measuring time, where N is a natural number.

In a preferred aspect of the present invention, the predetermined measuring time is a moving average time which is used in moving average performed on monitoring signals obtained by the sensor.

In a preferred aspect of the present invention, the method further includes detecting a polishing end point by the monitoring of the surface state of the workpiece by the sensor.

In a preferred aspect of the present invention, during the monitoring of the surface state of the workpiece by the sensor, polishing of the workpiece is performed so as to provide a uniform film thickness of the surface of the workpiece.

In a preferred aspect of the present invention, the predetermined measuring time is a time required for the polishing table to make a predetermined number of revolutions which is selected from among natural numbers from 4 to 16×V, where V represents the rotational speed of the polishing table.

Another aspect of the present invention provides a polishing method including: holding and rotating a workpiece by a top ring; pressing the workpiece against a polishing surface on a rotating polishing table to polish the workpiece; and monitoring a surface state of the workpiece with a sensor provided on the polishing table during polishing of the workpiece. A rotational speed of the top ring and a rotational speed of the polishing table are set such that, while the polishing table makes a predetermined number of revolutions which is expressed by a first natural number, the top ring makes a predetermined number of revolutions which is expressed by a second natural number, the first natural number and the second natural number are relatively prime, and the first natural number is not less that 4 and not more than a number of revolutions the polishing table makes within 16 seconds.

Another aspect of the present invention provides a polishing method including: holding and rotating a workpiece by a top ring; pressing the workpiece against a polishing surface on a rotating polishing table to polish the workpiece; and monitoring a surface state of the workpiece with a sensor provided on the polishing table during polishing of the workpiece. A rotational speed of the top ring and a rotational speed of the polishing table satisfy a relational expression given by $$n \cdot V/m - 1 \leq R \leq n \cdot V/m + 1 \text{ or } m \cdot R/n - 1 \leq V \leq m \cdot R/n + 1$$

where V is the rotational speed of the polishing table and is a natural number indicating a multiple of a setting unit that is allowed by a polishing apparatus, R is the rotational speed of the top ring and is a natural number indicating a multiple of the setting unit that is allowed by the polishing apparatus, m is a predetermined natural number that indicates the number of revolutions the polishing table makes while the sensor travels across the surface of the workpiece in directions or orientations distributed evenly in a circumferential direction of the workpiece over an entire circumference thereof, and n is a natural number such that m and n are relatively prime.

Another aspect of the present invention provides a polishing apparatus including: a top ring configured to hold and rotate a workpiece; a rotatable polishing table having a polishing surface, the top ring being configured to press the workpiece against the polishing surface; and a sensor provided on the polishing table and configured to monitor a surface state of the workpiece during polishing of the workpiece. A rotational speed of the top ring and a rotational speed of the polishing table are set such that paths of the sensor, described on a surface of the workpiece in a predetermined measuring time, are distributed substantially evenly over an entire circumference of the surface of the workpiece.

Another aspect of the present invention provides a polishing apparatus including: a top ring configured to hold and rotate a workpiece; a rotatable polishing table having a polishing surface, the top ring being configured to press the workpiece against the polishing surface; and a sensor provided on the polishing table and configured to monitor a surface state of the workpiece during polishing of the workpiece. A rotational speed of the top ring and a rotational speed of the polishing table are set such that, while the polishing table makes a predetermined number of revolutions which is expressed by a first natural number, the top ring makes a predetermined number of revolutions which is expressed by a second natural number, the first natural number and the second natural number are relatively prime, and the first natural number is not less that 4 and not more than a number of revolutions the polishing table makes within 16 seconds.

Another aspect of the present invention provides a polishing apparatus including: a top ring configured to hold and rotate a workpiece; a rotatable polishing table having a polishing surface, the top ring being configured to press the workpiece against the polishing surface; and a sensor provided on the polishing table and configured to monitor a surface state of the workpiece during polishing of the workpiece. A rotational speed of the top ring and a rotational speed of the polishing table satisfy a relational expression given by $$n \cdot V/m-1 \leq R \leq n \cdot V/m+1 \text{ or } m \cdot R/n-1 \leq V \leq m \cdot R/n+1$$

where V is the rotational speed of the polishing table and is a natural number indicating a multiple of a setting unit that is allowed by a polishing apparatus, R is the rotational speed of the top ring and is a natural number indicating a multiple of the setting unit that is allowed by the polishing apparatus, m is a predetermined natural number that indicates the number of revolutions the polishing table makes while the sensor travels across the surface of the workpiece in directions or orientations distributed evenly in a circumferential direction of the workpiece over an entire circumference thereof, and n is a natural number such that m and n are relatively prime.

Another aspect of the present invention provides a polishing apparatus including: a top ring configured to hold and rotate a workpiece; a rotatable polishing table having a polishing surface, the top ring being configured to press the workpiece against the polishing surface; a sensor provided on the polishing table and configured to monitor a surface state of the workpiece during polishing of the workpiece; and a monitoring device configured to process signal from the sensor. A rotational speed of the top ring and a rotational speed of the polishing table are set such that the sensor travels across a surface of the workpiece in a different path every time the sensor scans the surface of the workpiece, and the monitoring device is configured to calculate an average of signal values obtained along plural paths of the sensor which rotate around the surface of the workpiece and provide a set of sensor paths.

According to the present invention, by adjusting the rotational speed of the polishing table and the rotational speed of the top ring, the sensor does not scan only local areas, but scans substantially the entire surface of the workpiece evenly in the predetermined measuring time. As a result, an average film thickness can be grasped while an influence of noise is suppressed. Therefore, an accurate polishing end point detection and uniform film thickness can be realized.

BRIEF DESCRIPTION OF DRAWINGS

FIG. 27 is a table showing examples of a ratio R/V of the rotational speeds of the top ring and the polishing table which satisfies an equation (9).

BEST MODE FOR CARRYING OUT THE INVENTION

Embodiments of the present invention will be described in detail below with reference to the drawings.

Figure 1:
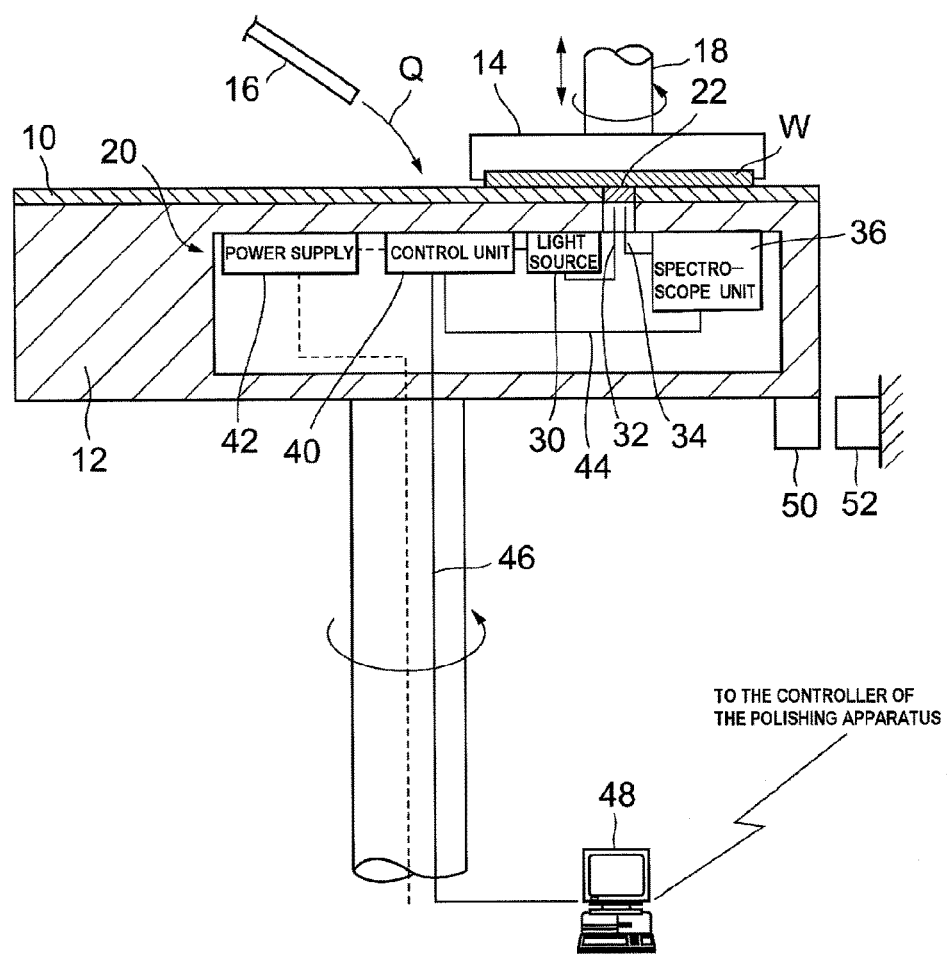
FIG. 1 is a schematic view showing an overall arrangement of a polishing apparatus capable of performing a method of detecting a polishing end point according to an embodiment of the present invention.

FIG. 1 is a schematic view showing an overall arrangement of a polishing apparatus capable of performing a method of detecting a polishing end point according to an embodiment of the present invention. As shown in FIG. 1, the polishing apparatus has a polishing table 12 with a polishing pad 10 attached to an upper surface thereof, and a top ring 14 for holding a substrate W, which is a workpiece (object to be polished) and pressing the substrate W against an upper surface of the polishing pad 10. The upper surface of the polishing pad 10 serves as a polishing surface providing a sliding contact with the substrate W. An upper surface of a fixed abrasive plate containing fine abrasive particles (made of $CeO_2$ or the like) fixed by a binder, such as resin, may be used as a polishing surface.

The polishing table 12 is coupled to a motor (not shown) disposed therebelow, and is rotatable about its own axis as indicated by arrow. A polishing liquid supply nozzle 16 is disposed above the polishing table 12 and supplies a polishing liquid Q onto the polishing pad 10.

The top ring 14 is coupled to a top ring shaft 18, which is coupled to a motor and an elevating cylinder (not shown). The top ring 14 can thus be vertically moved as indicated by arrow and rotated about the top ring shaft 18. The substrate W as the object of polishing is attracted to and held on a lower surface of the top ring 14 by a vacuum suction or the like. With this arrangement, the top ring 14 can press the substrate W held on its lower surface against the polishing pad 10 at a desired pressure, while rotating about its own axis.

In the polishing apparatus of the above construction, the substrate W held on the lower surface of the top ring 14 is pressed against the polishing pad 10 on the upper surface of the rotating polishing table 12. The polishing liquid Q is supplied onto the polishing pad 10 from the polishing liquid supply nozzle 16. The substrate W is thus polished with the polishing liquid Q being present between the surface (lower surface) of the substrate W and the polishing pad 10.

The polishing table 12 has a polishing state monitoring apparatus 20 embedded therein for monitoring a polishing state of the substrate W during polishing of the substrate W.

This polishing state monitoring apparatus 20 is configured so as to monitor, continuously in real-time, a polishing situation (a thickness and a state of the remaining film) on the surface of the substrate W during polishing of the substrate W. A light transmission unit 22 for transmitting light from the polishing state monitoring apparatus 20 therethrough is attached to the polishing pad 10. The light transmission unit 22 is made of a material of high transmittance, e.g., non-foamed polyurethane or the like. Alternatively, the light transmission unit 22 may be in the form of a transparent liquid flowing upwardly into a through-hole that is formed in the polishing pad 10. In this case, the liquid is supplied into the through-hole while the through-hole is being closed by the substrate W. The light transmission unit 22 may be located in any position on the polishing table 12 as long as it can travel across the surface of the substrate W held by the top ring 14. However, it is preferable that the light transmission unit 22 be located in a position where it passes through a center of the substrate W.

As shown in FIG. 1, the polishing state monitoring apparatus 20 includes a light source 30, a light-emitting optical fiber 32 serving as a light-emitting unit for applying light from the light source 30 to the surface of the substrate W, a light-receiving optical fiber 34 serving as a light-receiving unit for receiving reflected light from the surface the substrate, a spectroscope unit 36 having a spectroscope for dividing light received by the light-receiving optical fiber 34 and a plurality of photodetectors for converting the light, divided by the spectroscope, into electrical information and storing the resultant electrical information, a control unit 40 for controlling energization and de-energization of the light source 30 and a timing to start a reading process of the photodetectors of the spectroscope unit 36, and a power supply 42 for supplying electric power to the control unit 40. The light source 30 and the spectroscope unit 36 are supplied with electric power through the control unit 40.

The light-emitting optical fiber 32 and the light-receiving optical fiber 34 have a light-emitting end and a light-receiving end, respectively, which are arranged to be substantially perpendicular to the surface of the substrate W. The light-emitting optical fiber 32 and the light-receiving optical fiber 34 are arranged so as not to project upwardly from the surface of the polishing table 12 in consideration of replacement work for the polishing pad 10 and the quantity of light received by the light-receiving optical fiber 34. The photodetectors of the spectroscope unit 36 may comprise an array of 512 photodiodes.

The spectroscope unit 36 is coupled to the control unit 40 via a cable 44. The information from the photodetectors of the spectroscope unit 36 is transmitted to the control unit 40 via the cable 44. Based on the information, the control unit 40 generates spectral data of the reflected light. Specifically, the control unit 40 according to the present embodiment serves as a spectral data generator configured to read the electrical information stored in the photodetectors and generate spectral data of the reflected light. A cable 46 extends from the control unit 40 through the polishing table 12 to a processor 48, which is a personal computer, for example. The spectral data generated by the spectral data generator of the control unit 40 are transmitted to the processor 48 through the cable 46.

Based on the spectral data received from the control unit 40, the processor 48 calculates a characteristic value of the surface of the substrate W. The characteristic value is an index indicating a polishing state of the surface of the substrate. The processor 48 also has a function to receive information as to polishing conditions from a controller (not shown) which controls the polishing apparatus, and a function to determine a polishing end point (stop of polishing or a change of polishing conditions) based on time variation of the calculated characteristic value and send a command to the controller of the polishing apparatus.

As shown in FIG. 1, a proximity sensor 50 is mounted on a lower end of the polishing table 12 in a position near its circumferential edge, and a dog 52 is mounted outwardly of the polishing table 12 in alignment with the proximity sensor 50. Each time the polishing table 12 makes one revolution, the proximity sensor 50 detects the dog 52 to thereby determine a rotation angle of the polishing table 12.

The light source 30 comprises a light source configured to emit light having a wavelength range including white light. For example, a pulsed light source, such as a xenon lamp, can be used as the light source 30. When the pulsed light source is used as the light source 30, the light source 30 emits pulsed light at each measuring point according to a trigger signal during a polishing process. Alternatively, a tungsten lamp may be used as the light source 30. In this case, the light source 30 may emit light continuously at least when the light-emitting end of the light-emitting optical fiber 32 and the light-receiving end of the light-receiving optical fiber 34 are facing the surface of the substrate W.

Light from the light source 30 travels through the light-emitting end of the light-emitting optical fiber 32 and the light transmission unit 22, and is applied to the surface of the substrate W. The light is reflected off the surface, being polished, of the substrate W, passes through the light transmission unit 22, and is received by the light-receiving optical fiber 34 of the polishing state monitoring apparatus. The light, received by the light-receiving optical fiber 34, is transmitted to the spectroscope unit 36, which divides the light into a plurality of light rays according to wavelengths. The divided light rays having respective wavelengths are applied to the photodetectors corresponding to the wavelengths, and the photodetectors store electric charges according to quantities of the light rays applied. The electrical information stored in the photodetectors is read (released) at a predetermined timing, and converted into a digital signal. The digital signal is sent to the spectral data generator of the control unit 40, and the control unit 40 generates spectral data corresponding to respective measuring points.

Figure 2:
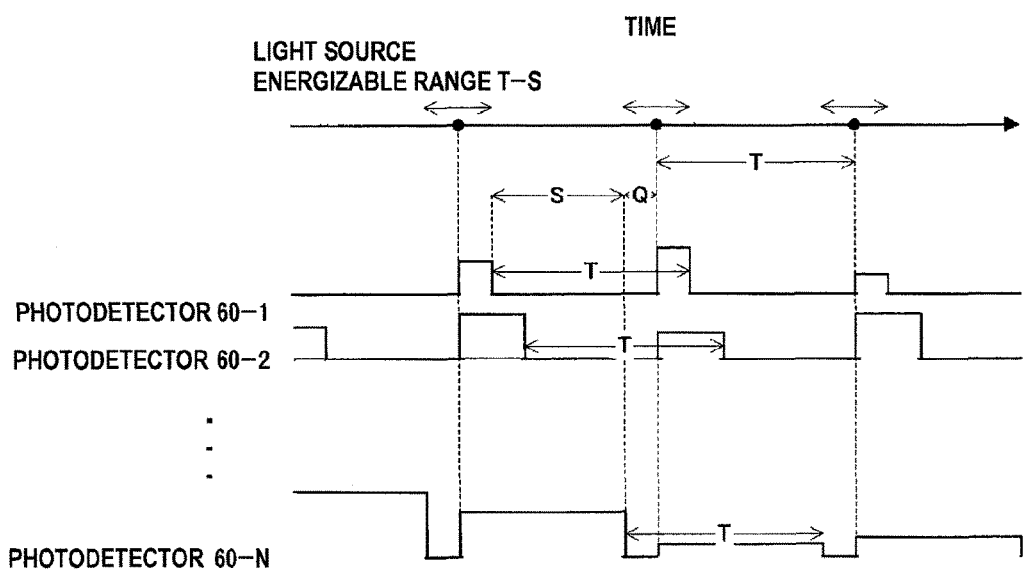
FIG. 2 is a diagram showing the operation of light-receiving elements in a spectroscope unit in a case where a pulsed light source is used in the polishing state monitoring apparatus shown in FIG. 1.
Figure 3:
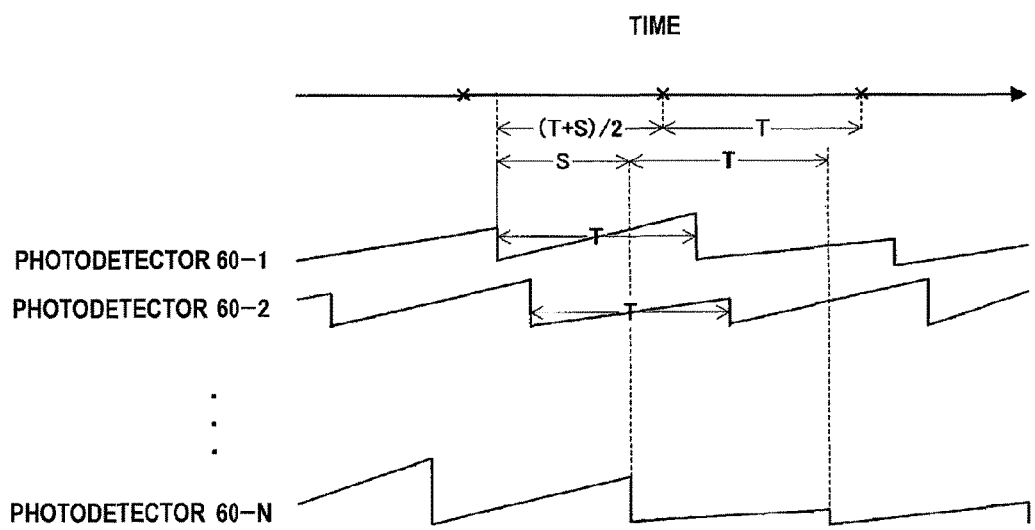
FIG. 3 is a diagram showing the operation of light-receiving elements in a spectroscope unit in a case where a continuous light source is used in the polishing state monitoring apparatus shown in FIG. 1.

Operation of the photodetectors of the spectroscope unit 36 will be described below. FIGS. 2 and 3 are diagrams showing an operating manner of the photodetectors in a case where the spectroscope unit 36 has photodetectors 60-1 through 60-N (the total number is N). More specifically, FIG. 2 shows a case where the pulsed light source is used as the light source 30, and FIG. 3 shows a case where the continuous light source is used as the light source 30. In FIGS. 2 and 3, horizontal axis represents time, and rising portions of graphs show that the electrical information is stored in the photodetectors, and falling portions show that the electrical information is read (released) from the photodetectors. In FIG. 2, black circles (●) indicate times when the pulsed light source is turned on.

In one sampling cycle, the photodetectors 60-1 through 60-N are successively switched from one to another to read (release) the electrical information therefrom. As described above, the photodetectors 60-1 through 60-N store the quantities of light rays of the corresponding wavelengths as the electrical information, and the stored electrical information is repeatedly read (released) from the photodetectors 60-1 through 60-N at a sampling period T with phase difference therebetween. The sampling period T is set to be relatively small, insofar as sufficient quantities of light are stored as electrical information in the photodetectors 60-1 through 60-N and data read from the photodetectors 60-1 through 60-N can sufficiently be processed in real-time. When an array of 512 photodiodes is used as the photodetectors, the sampling period T is on the order of 10 milliseconds. In FIGS. 2 and 3, S represents a time from when the first photodetector 60-1 is read to when the last photodetector 60-N is read, where S<T. In the case of FIG. 2, the time (indicated by ● in FIG. 2) when the pulsed light source is turned on is a sampling time. In the case of FIG. 3, the time (indicated by "x" in FIG. 3) that is half the time after the first photodetector 60-1 is read and starts storing new electrical information until the last photodetector 60-N is read is a sampling time for corresponding measuring areas. Points on the substrate W which face the light transmission unit 22 at the sampling times will be referred to as sampling points.

In FIG. 2, all the photodetectors 60-1 through 60-N store light while the light source 30 lights up instantaneously (for about several microseconds). Where Q represents the time from when the electrical information stored in the last photodetector 60-N is read (released) to when the light source 30 is turned on, if the light source 30 is tuned on before the electrical information stored in the first photodetector 60-1 is read (released), an inequality 0<Q<T−S holds. While Q can take any value within the range indicated by the above inequality, the following descriptions use a value of Q=(T−S)/2. The first photodetector 60-1 is read and starts storing new electrical information at a timing that is earlier than the sampling time by S+Q, i.e., (T+S)/2. In FIG. 3, the first photodetector 60-1 is also read at a timing that is earlier than the sampling time by (T+S)/2. With respect to the continuous light source shown in FIG. 3, the photodetectors 60-1 through 60-N start storing electrical information at different times, and the stored electrical information is read from the photodetectors 60-1 through 60-N at different times. Consequently, actual measuring areas slightly vary depending on the wavelengths.

Figure 4:
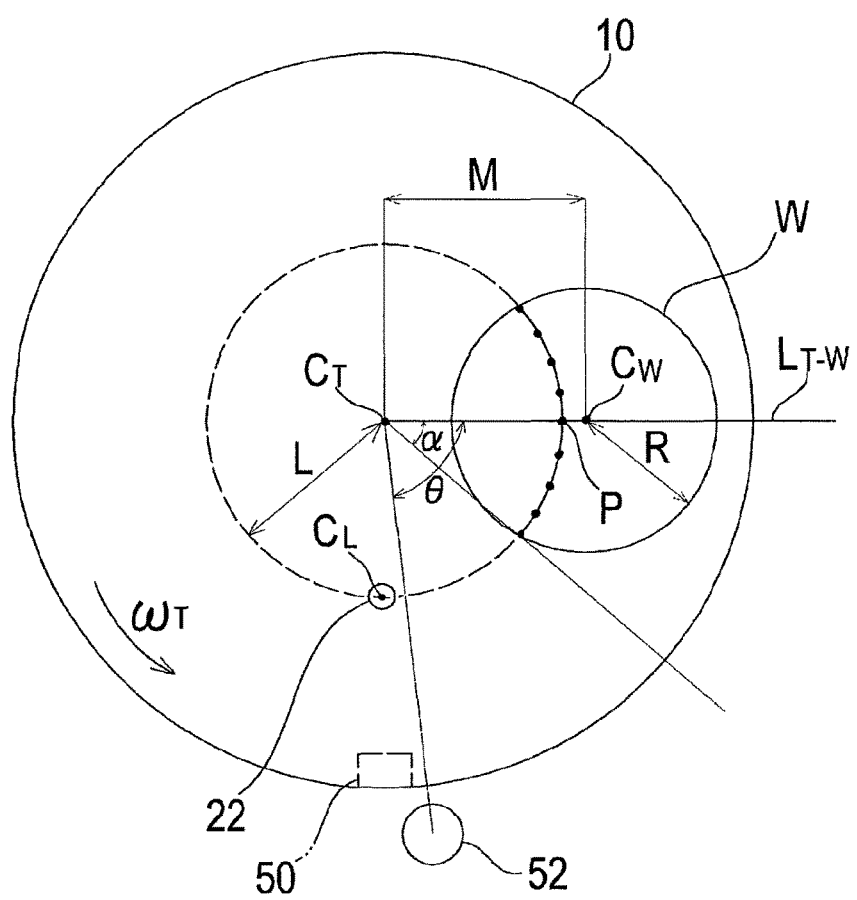
FIG. 4 is a plan view illustrative of sampling timings of the polishing state monitoring apparatus shown in FIG. 1.

Next, processes of determining a sampling timing by the polishing state monitoring apparatus 20 will be described. First, a process of determining a sampling timing in a case of using the pulsed light source will be described. FIG. 4 is a view illustrative of sampling timings of the polishing state monitoring apparatus 20. Each time the polishing table 12 makes one revolution, the proximity sensor 50 disposed on the circumferential edge of the polishing table 12 detects the dog 52 which serves as a reference position for operation of the proximity sensor 50. Specifically, as shown in FIG. 4, a rotation angle is defined as an angle, in a direction opposite to a direction of rotation of the polishing table 12, from a line $L_{T\text{-}W}$ (hereinafter referred to as a substrate center line) that interconnects the center $C_T$ of rotation of the polishing table 12 and the center $C_W$ of the substrate W. The proximity sensor 50 detects the dog 52 when the rotation angle is θ. The center $C_W$ of the substrate W can be specified by controlling the position of the top ring 14.

As shown in FIG. 4, where a horizontal distance between the center $C_T$ of the polishing table 12 and the center $C_L$ of the light transmission unit 22 is represented by L, a horizontal distance between the center $C_T$ of the polishing table 12 and the center $C_W$ of the substrate W is represented by M, a radius of a measuring target surface of the substrate W which is the surface, to be polished, of the substrate W excluding an edge cut region thereof is represented by R, and an angle at which the light transmission unit 22 scans the measuring target surface of the substrate W is represented by 2*a*, the following equation (1) holds based on the cosine theorem, and the angle α can be determined from the following equation (1).

$$\alpha = \cos^{-1}\left(\frac{L^2 + M^2 - R^2}{2LM}\right) \quad (1)$$

In the present embodiment, sampling timings are adjusted such that a point P on the substrate center line $L_{T-W}$ through which the light transmission unit 22 passes is always selected as a sampling point. Where the number of sampling points on one side of the substrate center line $L_{T-W}$ is n (which is an integer), the number of all sampling points when the light transmission unit 22 scans the measuring target surface of the substrate W is expressed by 2n+1, including the sampling point P on the substrate center line $L_{T-W}$.

If a circumferential portion of the top ring 14 is located outwardly of the substrate W so as to block background light, the condition for the light transmission unit 22 to be present within the measuring target surface of the substrate W at a first sampling time can be expressed by the following inequality (2), where $\omega_T$ represents an angular velocity of the polishing table 12. The integer n which satisfies this condition can be obtained from the following inequality (2).

$$\alpha - \omega_T T \leq n\omega_T T < \alpha$$

That is, $$\frac{\alpha}{\omega_T T} - 1 \leq n < \frac{\alpha}{\omega_T T} \quad (2)$$

If the light transmission unit 22 and the proximity sensor 50 are located at the same angle with respect to the center $C_T$ of the polishing table 12, a time $t_S$ from when the proximity sensor 50 detects the dog 52 to when the first photodetector 60-1 starts storing electrical information in the first sampling cycle while the polishing table 12 makes one revolution, i.e., a sampling start time $t_S$, can be determined from the following equation (3).

$$t_S = \frac{\theta}{\omega_T} - \left(nT + \frac{T+S}{2}\right) \quad (3)$$
$$= \frac{\theta}{\omega_T} - \left(n + \frac{1}{2}\right)T - \frac{S}{2}$$

In order to reliably clear the quantity of light stored in the photodetectors while the light transmission unit 22 is located outside of the surface, being polished, of the substrate W, the data acquired in the first sampling cycle may be discarded. In this case, the sampling start time $t_S$ can be determined from the following equation (4).

$$t_S = \frac{\theta}{\omega_T} - \left(nT + \frac{T+S}{2} + T\right) \quad (4)$$
$$= \frac{\theta}{\omega_T} - \left(n + \frac{3}{2}\right)T - \frac{S}{2}$$

The polishing state monitoring apparatus 20 starts its sampling operation based on the sampling start time $t_S$ thus determined. Specifically, the control unit 40 starts pulse lighting of the light source 30 after elapse of the time $t_S$ from the detection of the dog 52 by the proximity sensor 50, and controls the operation timing of the photodetectors of the spectroscope unit 36 so as to repeat a sampling operation on a cycle of the sampling period T. Reflection spectral data at each sampling point are generated by the spectral data generator of the control unit 40 and is transmitted to the processor 48. Based on the spectral data, the processor 48 determines a characteristic value of the surface, being polished, of the substrate W.

In the present embodiment, since the point P on the substrate center line $L_{T-W}$ which is on the path of the light transmission unit 22 is always selected as a sampling point, the characteristic value at a given radial position on the surface of the substrate can repeatedly be measured each time the polishing table 12 makes one revolution. If the sampling period is constant, then the radial positions of measuring points on the surface of the substrate per revolution of the polishing table 12 become constant. Therefore, this measuring process is more advantageous in recognizing the situation of a remaining film on the substrate W than the case where the characteristic values at unspecific positions are measured. In particular, if the light transmission unit 22 is arranged so as to pass through the center $C_W$ of the substrate W, then the center $C_W$ of the substrate W is always measured as a fixed point each time the polishing table 12 makes one revolution. Therefore, a more accurate grasp of a time variation of a remaining film situation of the substrate W can be realized.

If the continuous light source is used as the light source 30, since the respective photodetectors continuously store electrical information and start storing the electrical information at different times, the integer n is determined in a manner different from a pulsed light source. Specifically, when the first photodetector 60-1 starts storing electrical information, the light transmission unit 22 needs to be present in the measuring target surface of the substrate W. Therefore, the inequality for determining the integer n is given as follows.

$$\alpha - \omega_T T \leq n\omega_T T + \omega_T \frac{T+S}{2} < \alpha \quad (5)$$

That is, $$\frac{\left(\frac{\alpha}{\omega_T} - \frac{S}{2}\right)}{T} - \frac{3}{2} \leq n < \frac{\left(\frac{\alpha}{\omega_T} - \frac{S}{2}\right)}{T} - \frac{1}{2}$$

The integer n can be determined from the above inequality (5), and the sampling start time $t_S$ can be determined based on the equation (3) or (4). As well as the case of using the pulsed light source, the polishing state monitoring apparatus 20 starts its sampling process based on the determined sampling start time $t_S$, and determines a characteristic value of the surface, being polished, of the substrate W from spectral data at each sampling point. In the above example, certain conditions are established with respect to the timing of lighting the pulsed light source and the positional relationship between the light transmission unit 22 and the proximity sensor 50. Even if these conditions are not met, n and $t_S$ can similarly be determined.

Figure 5:
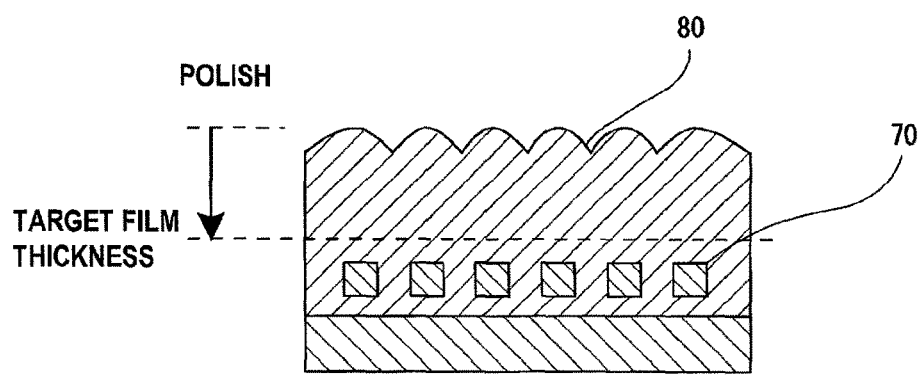
FIG. 5 is a cross-sectional view showing a sample substrate having an oxide film formed on metal interconnects.
Figure 6:
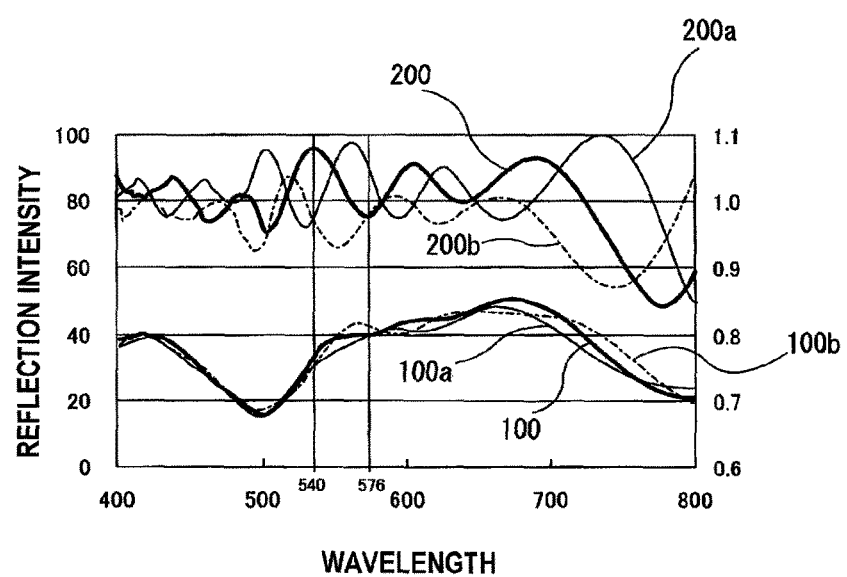
FIG. 6 is a graph showing spectral waveforms and reference spectral waveforms.

Next, a method of detecting a polishing end point from the spectral data at each sampling point will be described. FIG. 5 is a cross-sectional view showing a substrate (a reference workpiece) having an oxide film formed on metal interconnects. In this example, the oxide film 80 on the metal interconnects 70 is polished by a thickness of 800 nm (for 104 seconds), and reflection intensity during this polishing process is obtained as sample data. In FIG. 5, a target polishing end point is set to a time of 94 seconds. Reference numeral 100 in FIG. 6 represents a spectral waveform obtained at the time of 94 seconds. Reference numeral 100a and reference numeral 100b represent spectral waveforms each obtained at a polishing time other than the time of 94 seconds. A difference in shape between the spectral waveforms 100, 100a, and 100b indicates a difference in polishing time (i.e., a difference in film thickness). However, due to influences of device patterns or materials of underlying films, a basic shape of each spectral waveform is distorted greatly. This makes it difficult to recognize characteristics of a change in the reflection intensity as a result of a change in film thickness.

Thus, in order to remove the distortion of the basic shape of the spectral waveform, the spectral waveform 100 at the target film thickness (i.e., the polishing end point) of the reference workpiece is divided by reflection intensity averages, each of which is an average of reflection intensities at each wavelength within a polishing time, so that a reference spectral waveform is created. More specifically, the reflection intensities at each wavelength are averaged over the polishing time (in this example, 0 to 104 seconds), so that an average reflection intensity for each wavelength is determined. Then, each of the reflection intensities, indicated by the spectral waveform 100, is divided by the corresponding average reflection intensity at each wavelength, whereby the reference spectral waveform is obtained. In FIG. 6, a right vertical axis indicates a magnitude of the reference spectral waveform. Reference spectral waveforms 200, 200a, and 200b correspond to the spectral waveforms 100, 100a, and 100b. As can be seen from FIG. 6, compared with the spectral waveforms prior to normalization, the reference spectral waveforms have clearly distinguishable shapes reflecting the difference in film thickness. Moreover, local maximum points and local minimum points appear clearly. Thus, based on the reference spectral waveform 200 at the target film thickness, wavelengths of a local maximum value and a local minimum value are selected, and the characteristic value as an index of the film thickness is calculated from a combination of reflection intensities at the selected wavelengths. While each of the reflection intensities is divided by the corresponding average reflection intensity at each wavelength in this embodiment, the same result can also be obtained by subtracting each of the average reflection intensities from the corresponding reflection intensity at each wavelength. If the spectral waveform is not distorted, the local maximum point and the local minimum point may be determined from the spectral waveform, without creating the reference spectral waveforms.

Figure 7:
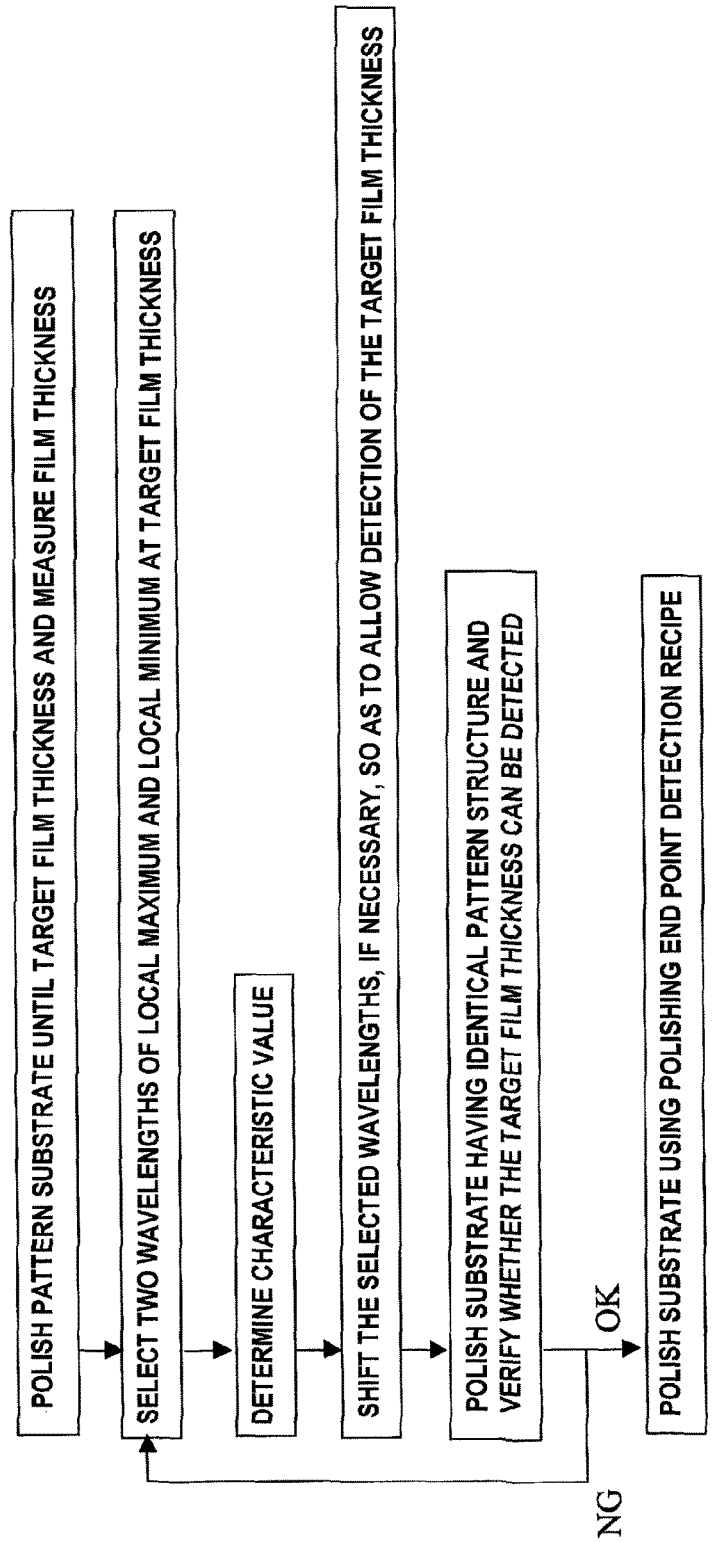
FIG. 7 is a flow diagram illustrating calculation of a characteristic value and selection of the wavelengths.

Next, the calculation of the characteristic value and the selection of the wavelengths will be described with reference to a flow diagram as shown in FIG. 7. First, the substrate (the reference workpiece) having pattern interconnects as shown in FIG. 5 is polished until the target film thickness is reached, and the film thickness is measured. Subsequently, two wavelengths of a local maximum value and a local minimum value are selected based on the reference spectral waveform of the polished substrate. Then, the characteristic value is determined from the reflection intensities at the selected two wavelengths. If necessary, the wavelengths to be selected may be shifted to longer wavelengths or shorter wavelengths so that fine adjustment of the characteristic value is made (this will be described in detail later). Next, a substrate identical to the reference workpiece is polished. From the results of polishing of this substrate, whether or not the characteristic value shows a distinctive point, i.e., whether or not the target film thickness can be detected by monitoring the time variation of the characteristic value is verified. If the target film thickness can be detected, the above-mentioned distinctive point is set as a polishing end point, and is used in the polishing end point detection in polishing of other substrates. These processes are performed in the processor 48.

The process of determining the characteristic value will be described with reference to a specific example. As shown in FIG. 6, a wavelength of 540 nm at which the reference spectral waveform 200 takes a local maximum value and a wavelength of 576 nm at which the reference spectral waveform 200 takes a local minimum value are selected. Then, a characteristic value X(t) is determined from the following equation.

$$X(t)=\rho_{540}(t)/(\rho_{540}(t)+\rho_{576}(t)) \quad (6)$$

In the above equation, ρ represents a reflection intensity and t represents a polishing time.

This characteristic value X(t) is used in polishing of a next substrate or a substrate to be polished after an arbitrary number of substrates are polished.

The above description is about the process of calculating the characteristic value from the reference spectral waveform of the reference workpiece. In another example, an average of the reflection intensities at each wavelength over the polishing time of the reference workpiece, may be used in a polishing process of a next substrate or a substrate to be polished after an arbitrary number of substrates are polished. Specifically, the reflection intensity, obtained in currently performed polishing of a substrate, is divided by the average of the refection intensities of the reference workpiece at each wavelength, so that a reference spectral waveform is obtained. This reference spectral waveform is monitored during polishing of the substrate in the same manner as described above, so that the polishing end point is determined based on the reference spectral waveform. As described above, since the reference spectral waveform has a distinguishable shape, an accurate polishing end point detection can be realized.

Figure 8:
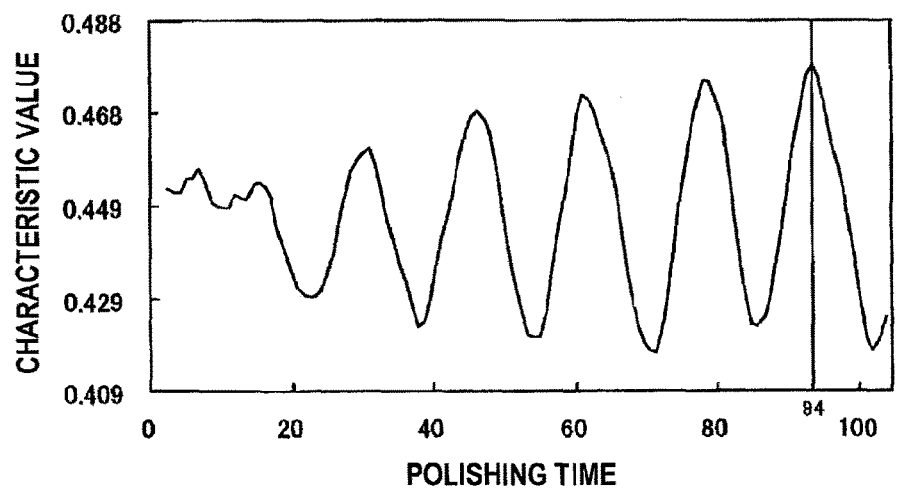
FIG. 8 is a graph showing a change in the characteristic value with time.

FIG. 8 is a graph showing a change with time in the characteristic value determined from the above-described equation (6). As can be seen from FIG. 8, a local maximum value of the characteristic value appears at a time of 94 seconds as intended. Therefore, this distinctive point at which the local maximum value appears is preset as a polishing end point, and a polishing process is terminated when the distinctive point is detected. After the detection of the distinctive point, a substrate may be over-polished for a predetermined period of time. As shown in FIG. 8, an initial stage of polishing in first 20 seconds is in a process of removing irregularities from a substrate. Therefore, the characteristic value is noisy and has fine extrema. Thus, the polishing end point detection may be such that monitoring of the characteristic value is started after an elapse of 25 seconds from a polishing start point and a polishing end point is determined when a fifth local maximum value, in this example, is detected.

When wavelengths of a largest local maximum value and a smallest local minimum value are selected as extremum wavelengths for determining the characteristic value, the characteristic value tends to fluctuate greatly. As a result, a good signal-to-noise ratio is obtained in most cases. However, depending on device structures, selection of the wavelengths of the largest local maximum value and the smallest local minimum value may not bring a best result. Thus, it is preferable to select several combinations of wavelengths from among plural extremum wavelengths, observe a shape of the characteristic value determined from each combination, and select extremum wavelengths which are such that a distinctive point appears clearly at a target film thickness. While two extremum wavelengths are extracted for determining the characteristic value in the above example, any number of extremum wavelengths can be extracted from among the extremum wavelengths obtained. Possible combinations of extremum wavelengths include $\rho_k/\rho_i$ and $(\rho_j + \ldots + \rho_{j+q})/(\rho_i + \ldots + \rho_{i+p})$.

In the above-described example, the characteristic value is calculated based on the time variation of the reflection intensities at the selected extremum wavelengths. Alternatively, as described in Japanese laid-open patent publication No. 2004-154928 (patent application No. 2003-321639), it is possible to determine the characteristic value by multiplying a weight function having a weight centered on the extremum wavelength by the spectral waveform. Normal distribution may be used as a shape of the weight function. The method of using such weight function will be described below.

Figure 9:
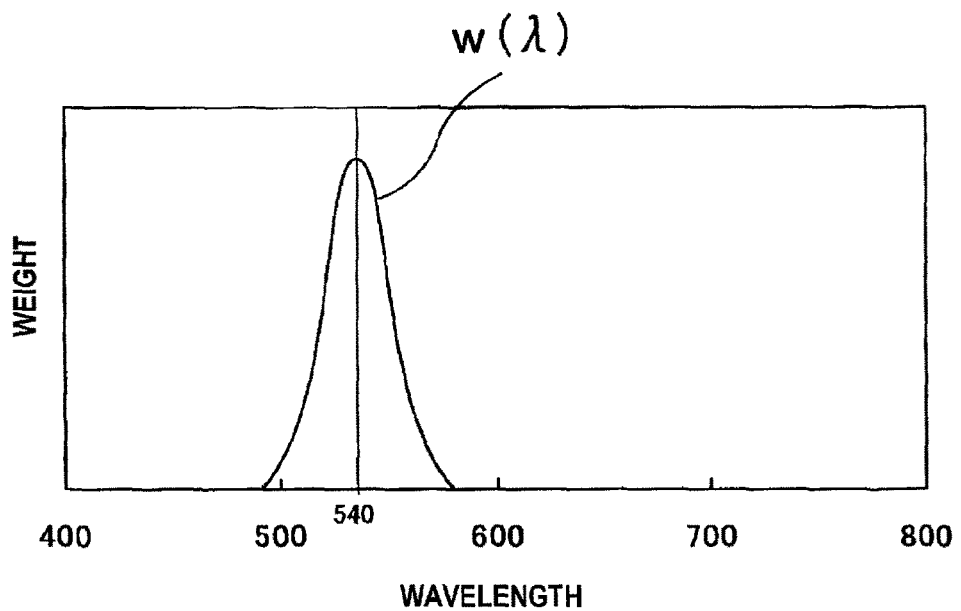
FIG. 9 is a graph showing a weight function.

First, a wavelength λ=540 nm, which shows a local maximum value, is selected based on the reference spectral waveform 200 at the polishing end point. Next, as shown in FIG. 9, a weight function w(λ) having a weight centered on this wavelength (540 nm) is defined in advance. Measurements ρ(λ) of reflection intensity of the reflected light from the surface of the substrate are multiplied by the weight function w(λ), and the resultant values are added, i.e., integrated into a scalar value. The resultant scalar value is defined as a characteristic value X. Specifically, the characteristic value X is defined according to the following equation (7).

$$X = \sum_\lambda w(\lambda)\rho(\lambda)\Delta\lambda \qquad (7)$$

Alternatively, plural weight functions $w_i(\lambda)$ (i=1, 2, ...) may be defined, and the characteristic value $X_i$ may be defined according to the following equation (8).

$$X_i = \frac{\sum_\lambda w_i(\lambda)\rho(\lambda)\Delta\lambda}{\sum_i \sum_\lambda w_i(\lambda)\rho(\lambda)\Delta\lambda} \qquad (8)$$

According to the method as described above, when a target film thickness is reached, i.e., when the polishing end point is reached, the characteristic value shows a distinctive changing point (distinctive point) such as a local maximum or a local minimum. Therefore, by monitoring the characteristic value during polishing and detecting the distinctive point of time variation of the characteristic value, the polishing end point (e.g., polishing stop point or a changing point of polishing conditions) can be determined. Further, according to the method as described above, even if a disturbance affects measurements of the reflection intensity at a certain wavelength, the influence of the disturbance is reduced because of the integration operation, compared with the case where the reflection intensity at the target film thickness is directly monitored.

The polishing end point detection method according to this embodiment is advantageous over the method disclosed in the Japanese laid-open patent publication No. 2004-154928 in the following respects. In the method of the patent publication No. 2004-154928, selection of a weight function that brings a distinctive change in the characteristic value at the target film thickness (i.e., the polishing end point) entails trial and error, which necessitate a lot of time. In addition, some weight functions may result in a bad SN ratio (signal-to-noise ratio), causing failure in a stable polishing end point detection. Furthermore, even when a film material to be polished and a film thickness are the same, the spectral waveform of the reflected light is affected by the difference in device pattern, type of underlying film, and device structure. In order to obtain a good result, it is necessary to define an optimum weight function for every different type of substrate, and as a result a productivity is lowered. According to the present embodiment, the reference spectral waveform having characteristic extrema can be obtained by dividing the reflection intensities by the average reflection intensities, and an optimum weight function can be easily determined.

Figure 10:
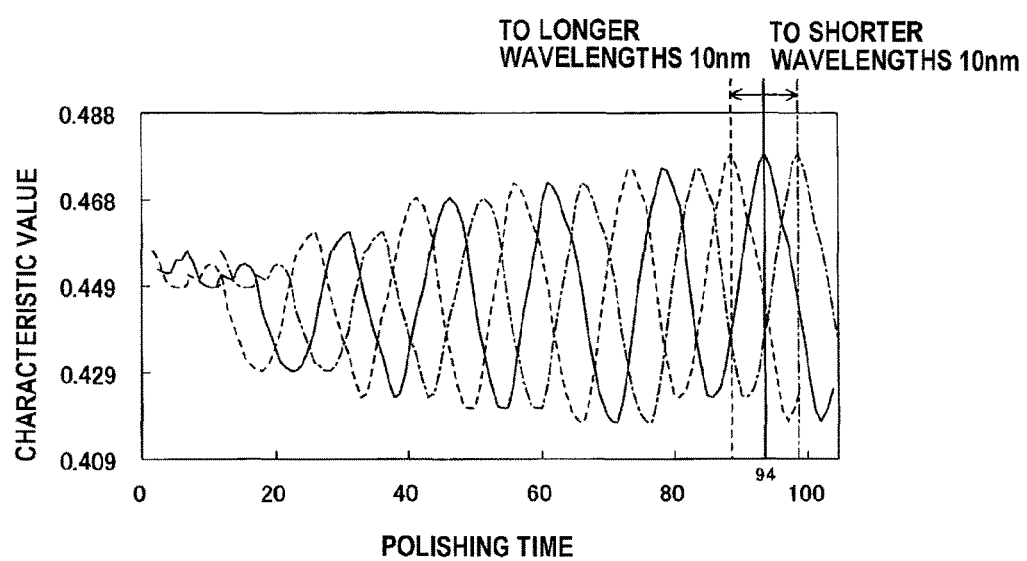
FIG. 10 is a graph showing the manner of change in a distinctive point when shifting the selected two wavelengths to longer wavelengths by 10 nm and to shorter wavelengths by 10 nm.

Excessive noise due to device patterns may cause not only the pre-normalization spectral waveform but also the distinctive point of the characteristic value, obtained from the normalized spectral waveform, to deviate from the target film thickness (i.e., the target polishing end time). In such a case, times of the extrema of the characteristic value can be adjusted by shifting the extremum wavelengths of the spectral waveform selected for calculation of the characteristic value. Therefore, it is preferable to reselect optimum wavelengths indicating a distinctive point at the polishing end point. When shifting the selected two wavelengths to longer wavelengths, an appearance time of the distinctive point of the characteristic value is shifted to shorter polishing times (i.e., larger film thicknesses). On the other hand, when shifting the selected two wavelengths to shorter wavelengths, an appearance time of the distinctive point of the characteristic value is shifted to longer polishing times (i.e., smaller film thicknesses). FIG. 10 is a graph showing the manner of change in the distinctive point when shifting the selected two wavelengths to longer wavelengths by 10 nm and to shorter wavelengths by 10 nm. According to the above-described way of determining the wavelengths for an approximate polishing end point, the distinctive point of the characteristic value is easily matched to the polishing end point by fine adjustment of the selected wavelengths.

If a distinctive point of a change in the reflection intensity as a result of a change in the film thickness can be captured from the pre-normalization spectral waveform, the characteristic value can be determined from the wavelengths at which the pre-normalization spectral waveform has extrema. In a case where devices have a simple structure, a spectral waveform may be obtained from simulation calculation, as long as the simulation calculation can produce a satisfactory waveform at a predetermined film thickness from a practical standpoint.

As described above, according to the embodiment of the present invention, it is possible to obtain the characteristic value which has a distinctive changing point at the polishing end point and has a good signal-to-noise ratio depending on a device pattern of a substrate. Therefore, an accurate polishing end point can be detected. The above-described embodiment can be applied not only to a polishing method and a polishing apparatus, but also to a method and apparatus for etching away a film to a target thickness and a method and apparatus for forming a film to a target thickness.

Next, another embodiment of the present invention will be described.

Figure 11:
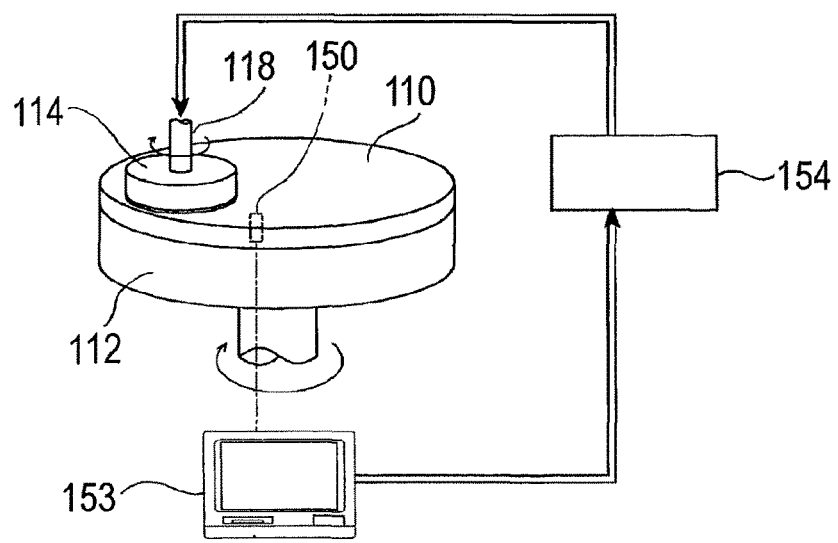
FIG. 11 is a schematic view showing a whole structure of a polishing apparatus according to another embodiment of the present invention.

FIG. 11 is a schematic view showing a whole structure of a polishing apparatus according to another embodiment of the present invention. As shown in FIG. 11, the polishing apparatus has a polishing table 112 supporting a polishing pad 110 attached to an upper surface thereof, and a top ring 114 configured to hold a substrate, which is a workpiece to be polished, and to press the substrate against an upper surface of the polishing pad 110. The upper surface of the polishing pad 110 provides a polishing surface with which the substrate is brought into sliding contact.

The polishing table 112 is coupled to a motor (not shown in the drawing) disposed therebelow, and is rotatable about its own axis as indicated by arrow. A polishing liquid supply nozzle (not shown in the drawing) is disposed above the polishing table 112, so that a polishing liquid is supplied from the polishing liquid supply nozzle onto the polishing pad 110.

The top ring 114 is coupled to a top ring shaft 118, which is coupled to a motor and an elevating cylinder (not shown in the drawing). The top ring 114 can thus be vertically moved and rotated about the top ring shaft 118. The substrate to be polished is attracted to and held on a lower surface of the top ring 114 by a vacuum suction or the like.

With the above-described structures, the substrate, held on the lower surface of the top ring 114, is rotated and pressed by the top ring 114 against the polishing surface of the polishing pad 110 on the rotating polishing table 112. The polishing liquid is supplied from the polishing liquid supply nozzle onto the polishing surface of the polishing pad 110. The substrate is polished in the presence of the polishing liquid between the surface (lower surface) of the substrate and the polishing pad 110.

Figure 12:
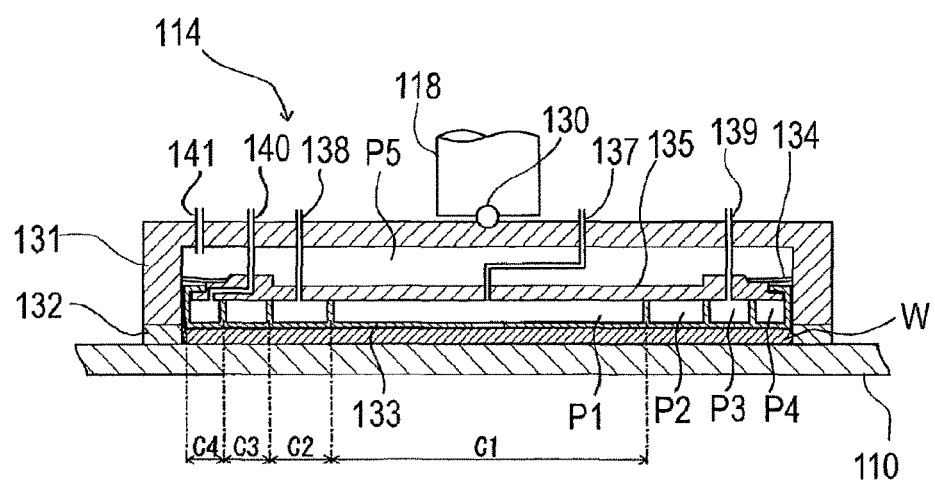
FIG. 12 is a schematic view showing a cross section of the top ring shown in FIG. 11.

FIG. 12 is a schematic view showing a cross section of the top ring shown in FIG. 11. As shown in FIG. 12, the top ring 114 has a disk-shaped top ring body 131 coupled to a lower end of the top ring shaft 118 via a flexible joint 130, and a retainer ring 132 provided on a lower portion of the top ring body 131. The top ring body 131 is made of a material having high strength and rigidity, such as metal or ceramic. The retainer ring 132 is made of highly rigid resin, ceramic, or the like. The retainer ring 132 may be formed integrally with the top ring body 131.

The top ring body 131 and the retainer ring 132 form therein a space, which houses an elastic pad 133 which is to be brought into contact with the substrate W, an annular pressure sheet 34 made from an elastic membrane, and a substantially disk-shaped chucking plate 135 configured to hold the elastic pad 133. The elastic pad 133 has an upper peripheral edge, which is held by the chucking plate 135. Four pressure chambers (air bags) P1, P2, P3, and P4 are provided between the elastic pad 133 and the chucking plate 135. A pressurized fluid (e.g., a pressurized air) is supplied into the pressure chambers P1, P2, P3, and P4 or a vacuum is developed in the pressure chambers P1, P2, P3, and P4 via fluid passages 137, 138, 139, and 140, respectively. The center pressure chamber P1 has a circular shape, and the other pressure chambers P2, P3, and P4 have an annular shape. These pressure chambers P1, P2, P3, and P4 are in a concentric arrangement.

A pressure-adjusting device (not shown in the drawing) is provided so as to change internal pressures of the pressure chambers P1, P2, P3, and P4 independently of each other to thereby substantially independently adjust pressing forces to be applied to four zones: a central zone C1, an inner middle zone C2, an outer middle zone C3, and a peripheral zone C4 (To be exact, each zone is more or less affected by the pressure chamber corresponding to the other zone, e.g., the adjacent zone). Further, by elevating or lowering the top ring 114 in its entirety, the retainer ring 132 can be pressed against the polishing pad 110 at a predetermined pressing force. A pressure chamber P5 is formed between the chucking plate 135 and the top ring body 131. A pressurized fluid is supplied into the pressure chamber P5 or a vacuum is developed in the pressure chamber P5 via a fluid passage 141. With this operation, the chucking plate 135 and the elastic pad 133 in their entirety can be moved vertically. The retainer ring 132 is arranged around the substrate W so as to prevent the substrate W from coming off the top ring 114 during polishing.

As shown in FIG. 11, a sensor 150 for monitoring (i.e., detecting) a state of a film of the substrate W is provided in the polishing table 112. This sensor 150 is coupled to a monitoring device 153, which is couple to a CMP controller 154. An eddy current sensor can be used as the sensor 150. An output signal of the sensor 150 is sent to the monitoring device 153. This monitoring device 153 performs necessary conversions and processing (calculations) on the output signal (sensing signal) of the sensor 150 to produce a monitoring signal. While a value of the monitoring signal (and the sensor signal) does not indicate a film thickness itself, the value of the monitoring signal changes according to the film thickness.

The monitoring device 153 also functions as a controller for operating the internal pressures of the pressure chambers P1, P2, P3, and P4 based on the monitoring signal, and also functions as a polishing end point detector for detecting a polishing end point. Specifically, the monitoring device 153 determines the pressing forces of the top ring 114 against the substrate W based on the monitoring signal. The determined pressing forces are sent to the CMP controller 154. The CMP controller 154 commands the non-illustrate pressure-adjusting device to change the pressing forces of the top ring 114 against the substrate W. The monitoring device 153 and the CMP controller 154 may be integrated into a single control device.

Figure 13:
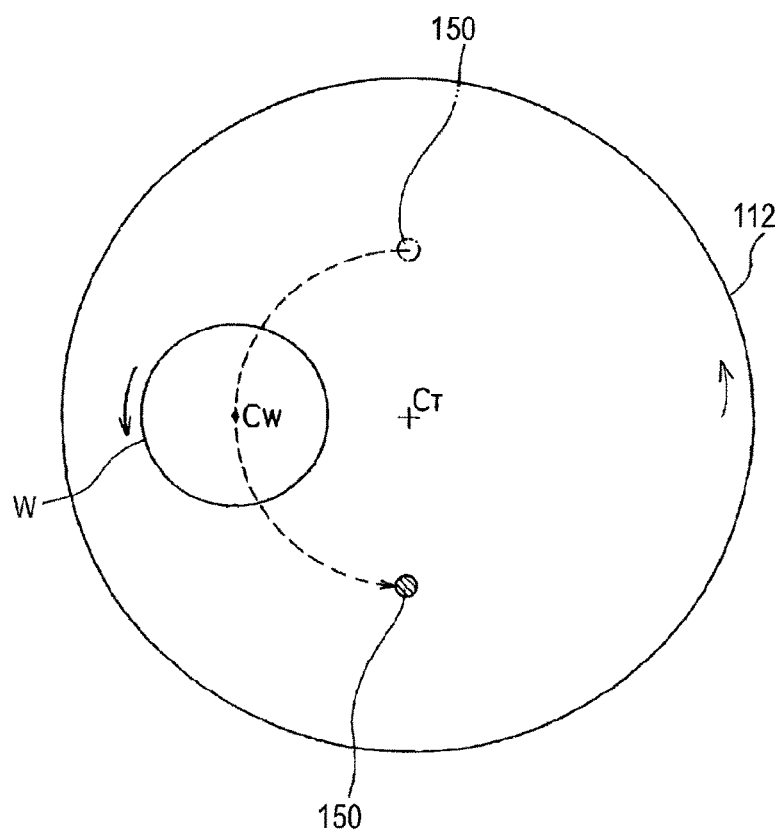
FIG. 13 is a plan view showing a positional relationship between a polishing table and a substrate.

FIG. 13 is a plan view showing a positional relationship between the polishing table 112 and the substrate W. As shown in FIG. 13, the sensor 150 is arranged in a location such that the sensor 150 passes through a center $C_W$ of the substrate W, held by the top ring 114, during polishing. A symbol $C_T$ is a center of rotation of the polishing table 112. While moving under the substrate W, the sensor 150 measures a thickness of a conductive film (e.g., a Cu layer) or a quantity that increases or decreases in accordance with a change in film thickness. The sensor 150 obtains measurements continuously along a path of its movement (i.e., a scan line).

Figure 14:
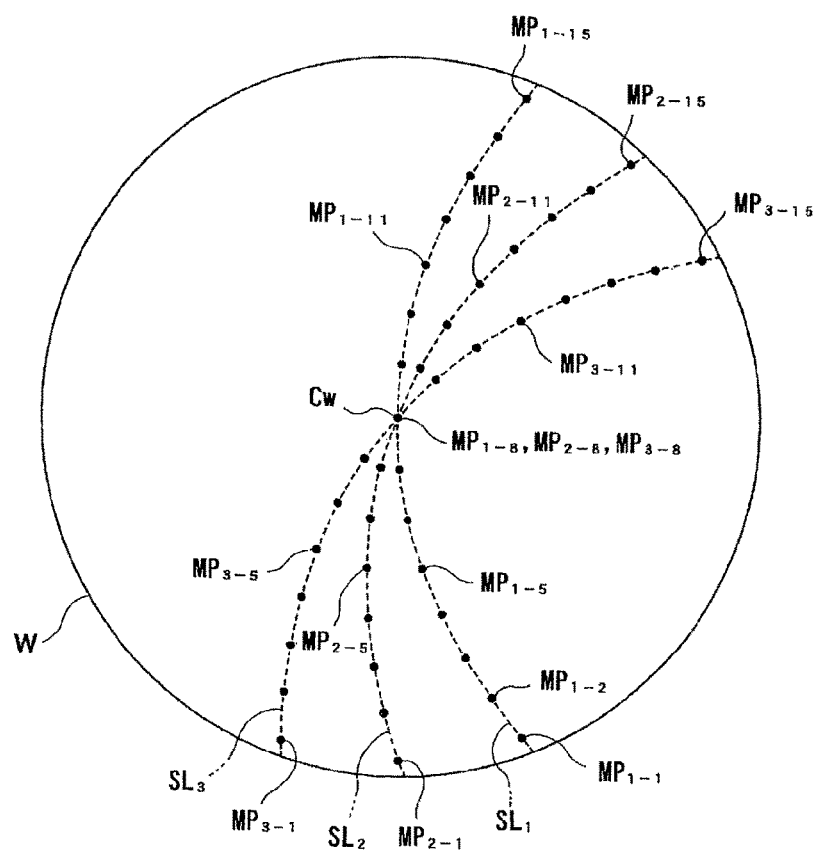
FIG. 14 is a view showing paths of a sensor sweeping across the substrate.

FIG. 14 is a view showing paths of the sensor 150 sweeping across the substrate W. The sensor 150 scans the surface (that is being polished) of the substrate W each time the polishing table 112 makes one revolution. Specifically, when the polishing table 112 is being rotated, the sensor 150 sweeps across the surface of the substrate W in a path passing through the center $C_W$ of the substrate W (center of the top ring shaft 118). A rotational speed of the top ring 114 is generally different from a rotational speed of the polishing table 112. Therefore, the path of the sensor 150 described on the surface of the substrate W changes as the polishing table 112 rotates, as indicated by scan lines $SL_1$, $SL_2$, $SL_3$, . . . in FIG. 14. Even in this case, since the sensor 150 is located so as to pass through the center $C_w$ of the substrate W as described above, the path of the sensor 150 passes through the center $C_w$ of the substrate W in every rotation. In this embodiment, measuring timings of the sensor 150 are adjusted so that the film thickness at the center $C_w$ of the substrate W is always measured by the sensor 150 in every rotation.

It is known that a polishing-rate profile of the substrate W is substantially axisymmetric with respect to an axis that extends through the center $C_w$ of the substrate W in a direction perpendicular to the surface of substrate W. Accordingly, as shown in FIG. 14, where an n-th measuring point on an m-th scan line $SL_m$ is represented by $MP_{m\text{-}n}$, the change in the film thickness of the substrate W at n-th measuring points, which define a radial position, can be monitored by tracking the monitoring signals obtained at the n-th measuring points $MP_{1\text{-}n}$, $MP_{2\text{-}n}$, . . . , $MP_{m\text{-}n}$ on respective scan lines.

In FIG. 14, for the sake of simplification, the number of measuring points in one scanning operation is set to 15. However, the number of measuring points is not limited to the illustrated example and various numbers can be set in accordance with a period of measuring operation and the rotational speed of the polishing table 112. When using an eddy current sensor as the sensor 150, no less than one hundreds of measuring points are generally set on one scan line. When a large number of measuring points are set in this manner, one of them substantially coincides with the center $C_w$ of the substrate W. Therefore, it is not necessary in this case to adjust the measuring timings with respect to the center $C_w$ of the substrate W.

Figure 15:
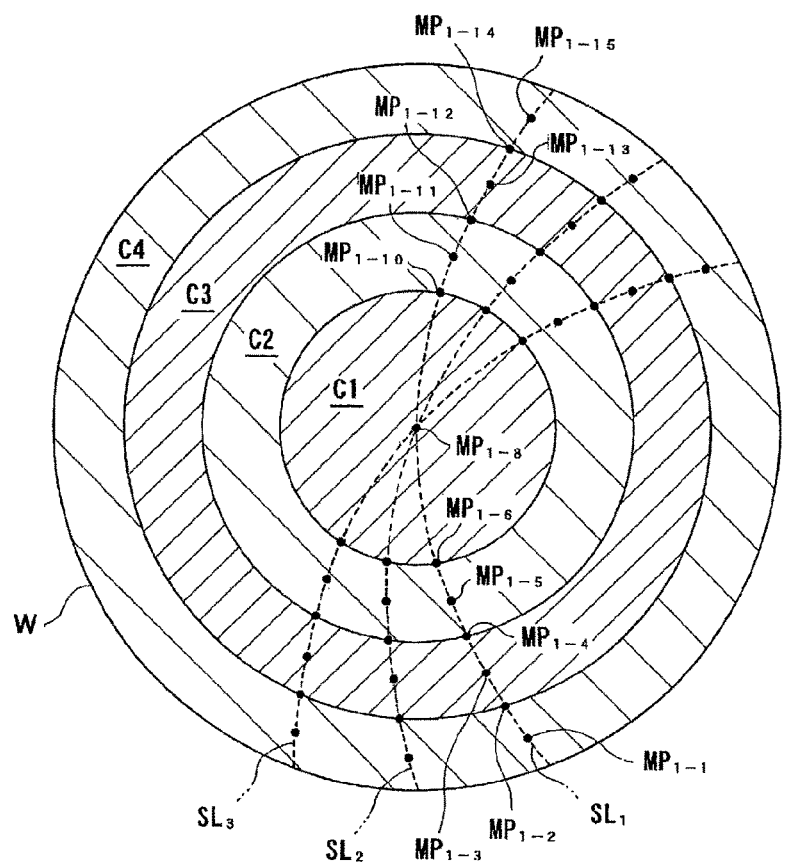
FIG. 15 is a plan view showing an example of selecting measuring points to be monitored by a monitoring device among the measuring points on the substrate shown in FIG. 14.

FIG. 15 is a plan view showing an example of selecting the measuring points to be monitored by the monitoring device 153, among the measuring points on the substrate W shown in FIG. 14. In the example shown in FIG. 15, the monitoring device 153 monitors the measuring points $MP_{m\text{-}1}$, $MP_{m\text{-}2}$, $MP_{m\text{-}3}$, $MP_{m\text{-}4}$, $MP_{m\text{-}5}$, $MP_{m\text{-}6}$, $MP_{m\text{-}8}$, $MP_{m\text{-}10}$, $MP_{m\text{-}11}$, $MP_{m\text{-}12}$, $MP_{m\text{-}13}$, $MP_{m\text{-}14}$, and $MP_{m\text{-}15}$ located near centers and boundaries of the zones C1, C2, C3, and C4 to which the pressing forces are applied independently. An additional measuring point may be provided between the measuring points $MP_{m\text{-}i}$ and $MP_{m\text{-}(i+1)}$, unlike the example shown in FIG. 14. Selecting of the measuring points to be monitored is not limited to the example shown in FIG. 15. Any point to be observed in view of polishing control of the surface of the substrate W can be selected as the measuring point to be monitored. All of the measuring points on each scan line can be selected.

The monitoring device 153 performs predetermined calculations on the output signal (sensing signal) of the sensor 150 obtained at the selected measuring points to produce the monitoring signals. Based on the monitoring signals and below-described reference signal, the monitoring device 153 calculates the internal pressures of the pressure chambers P1, P2, P3, and P4 in the top ring 114 corresponding to the respective zones C1, C2, C3, and C4. More specifically, the monitoring device 153 compares the monitoring signals, obtained at the selected measuring points, with the preset reference signal, and calculates optimum pressures in the pressure chambers P1, P2, P3, and P4 that can allow the respective monitoring signals to converge on the reference signal. The calculated pressure values are sent from the monitoring device 153 to the CMP controller 154, and the CMP controller 154 changes the pressures in the pressure chambers P1, P2, P3, and P4. In this manner, the pressing forces against the respective zones C1, C2, C3, and C4 of the substrate W are adjusted.

In order to eliminate noises so as to smoothen data, an average of the monitoring signals, obtained at neighboring measuring points, may be used. Alternatively, it is possible to calculate an average or a representative value of the monitoring signals obtained at the measuring points in each of the concentric zones which are divided according to the radial position from the center $C_w$ of the surface of the substrate W. In this case, the average or representative value can be used as a new monitoring signal for control. A distance of each measuring point from the center $C_w$ of the substrate W may be determined at each point of time during polishing, so that each measuring point is assigned to the proper zone based on the distance from the center $C_w$ of the substrate W. This operation is effective in a case where plural sensors are arranged along the radial direction of the polishing table 112 and in a case where the top ring 114 is configured to swing around the top ring head shaft 118.

Figure 16:
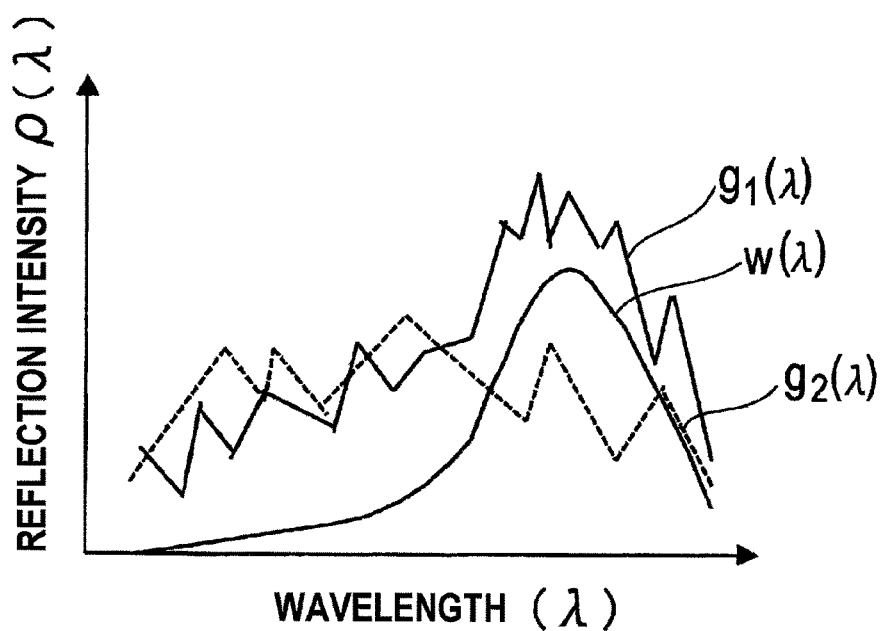
FIG. 16 is a graph showing the reflection intensity.

Next, a method of determining a polishing end point from the reflection intensities obtained at the respective measuring points using an optical sensor as the sensor 150 will be described based on the description of the Japanese laid-open patent publication No. 2004-154928.

Where a film to be polished is a light-transmissive thin film, such as an oxide film, with a uniform thickness and is in a disturbance-free ideal state, time variation of relative reflectances at respective wavelengths are as shown in FIG. 16 because of an interference caused by the film to be polished. Where the film has a refractive index n and a film thickness d and light has a wavelength λ (in vacuum), a film thickness difference corresponding to one period of the time variation is represented by $\Delta d = \lambda/2n$. Therefore, as the film thickness decreases linearly with the polishing time, the relative reflectance changes with time such that its local maximum value and local minimum value appear periodically, as shown in FIG. 16. In FIG. 16, a solid-line represents a relative reflectance at a wavelength λ=500 nm, and the broken-line represents a relative reflectance at a wavelength λ=700 nm.

With regard to the characteristic value determined by calculations including a multiplication that multiplies wavelength components of spectral data by the weight function, the characteristic value increases and decreases repetitively with the polishing time, i.e., with the decrease in film thickness, in a similar manner. In a case of pattern film, the characteristic value increases and decreases repetitively as well, although noise or distortion may appear on a waveform.

In monitoring of the characteristic value, the local maximum value and/or local minimum value of time variation of the characteristic value are detected, whereby the progress of polishing is shown. If the polishing process is stopped at the time an extremum is detected and the film thickness is measured as a reference, the progress of polishing can be associated with the thickness of the film being polished.

In detection of a polishing end point (stop point of polishing or a point of changing polishing conditions), an extremum (one of distinctive points) immediately before a desired film thickness is reached is detected, and the film is over-polished for a time which corresponds to the difference between the film thickness at the extremum and the desired film thickness.

The reflection intensities measured at the measuring points may be averaged each time the sensor 150 scans the surface of the substrate W, and the above-described characteristic value may be calculated from the resultant average. When the above-described series of processes are performed on the reflection intensity data for calculation of the characteristic value, it is preferable to perform moving average at a desirable stage in processing of the reflection intensity data. For example, it is possible to perform moving average on the reflection intensity data and then perform the above-described series of processes to determine the characteristic value. Alternatively, it is possible to perform moving average on the characteristic values calculated. Moving average is a process to average time-series data obtained in a predetermined time section (moving average time) while moving the time section.

Next, a path (scan line) of the sensor 150 when sweeping across the surface of the substrate will be described.

When the rotational speed of the polishing table and the rotational speed of the top ring are the same, a relative speed is the same at any point on the substrate, and the sensor, provided on the polishing table, passes through the same zone of the substrate every time the polishing table rotates. This is a logically-established fact. The rotational speeds of the polishing table and the top ring, however, cannot be exactly the same actually. In addition, if the polishing table and the top ring rotate at the same speed, the polishing table and the top ring are synchronized and this synchronized rotation can cause insufficient polishing in local zones due to an influence of grooves formed on the polishing pad. For these reasons, it has been customary to intentionally make a slight difference in rotational speed between the polishing table and the top ring.

Figure 17:
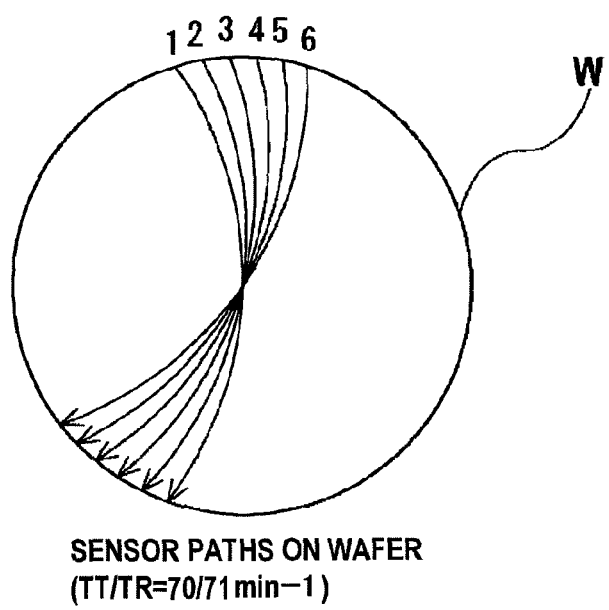
FIG. 17 is a view showing paths of the sensor described on the substrate in a case where a rotational speed of the polishing table is 70 $min^{-1}$ and a rotational speed of the top ring 114 is 71 $min^{-1}$.

FIG. 17 is a view showing paths of the sensor 150 described on the substrate W in a case where the rotational speed of the polishing table 112 is 70 min$^{-1}$ and the rotational speed of the top ring 114 is 71 min$^{-1}$.

Under these conditions, where the moving average time is set to 5 seconds, the sensor 150 can scan the substrate W six times during that period of time. In this case, the sensor path rotates only by an angle of 5.14 degrees each time the polishing table 112 makes one revolution. As a result, information on only a local portion of the substrate W is obtained, as shown in FIG. 17, resulting in failure in grasp of an accurate change in the reflection intensity with a change in film thickness.

Figure 18:
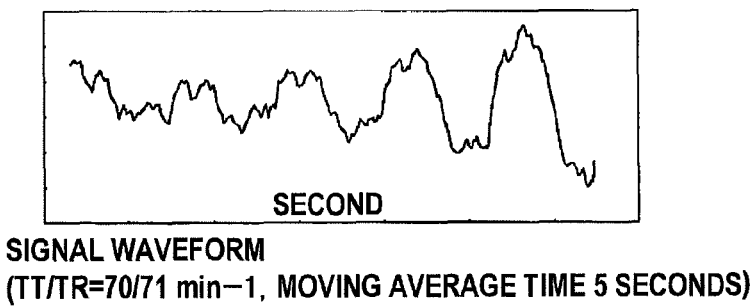
FIG. 18 is a graph showing a signal waveform of the characteristic value obtained under the conditions shown in FIG. 17.

FIG. 18 is a graph showing a signal waveform of the characteristic value obtained under the conditions shown in FIG. 17. Generally, the characteristic value obtained from the reflection intensity varies in a sine curve according to a change in film thickness because of interference of light. However, in the case where the rotational speed of the polishing table 112 is set to 70 min$^{-1}$, the rotational speed of the top ring 114 is set to 71 min$^{-1}$, and the moving average time is set to 5 seconds (six points with respect to moving average point), random noise appears on the signal waveform of the characteristic value, as shown in FIG. 18. As described previously, the polishing end point is generally determined based on detection of the local maximum value or local minimum value of the characteristic value. However, the extremum cannot be clearly captured due to the noise, or a time of the extremum may be shifted from the original polishing end time. In this case, an accurate polishing end point detection cannot be performed.

Figure 19:
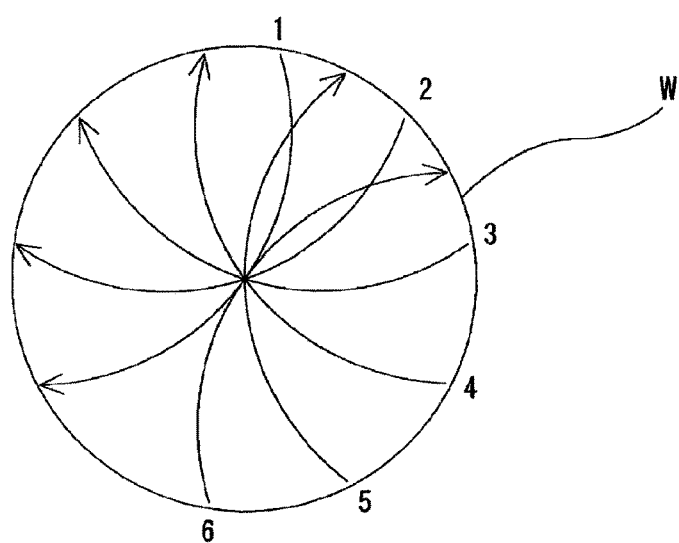
FIG. 19 is a view showing the paths of the sensor described on the substrate within a moving average time in the case where the rotational speed of the polishing table is 70 $min^{-1}$ and the rotational speed of the top ring is 77 $min^{-1}$.

Thus, in this invention, a ratio of the rotational speeds of the top ring 114 and the polishing table 112 is adjusted such that the paths of the sensor 150 described on the substrate W within a predetermined period of time (e.g., within the moving average time) are distributed substantially evenly over a circumference of the surface of the substrate W in its entirety. FIG. 19 is a view showing the paths of the sensor 150 described on the substrate within the moving average time (5 seconds in this example) in the case where the rotational speed of the polishing table 112 is 70 min$^{-1}$ and the rotational speed of the top ring 114 is 77 min$^{-1}$. As shown in FIG. 19, under these conditions, the path of the sensor 150 rotates by 36 degrees each time the polishing table 112 makes one revolution. Therefore, the path of the sensor 150 rotates by half of the circumference of the substrate W every time the sensor 150 scans five times. In view of a curvature of the sensor path, six-time sweep motions of the sensor 150 across the substrate W within the moving average time allow the sensor 150 to scan the entire surface of the substrate W substantially evenly. Therefore, the influence of areas with different pattern densities and different structures becomes substantially even in every moving average time.

Figure 20:
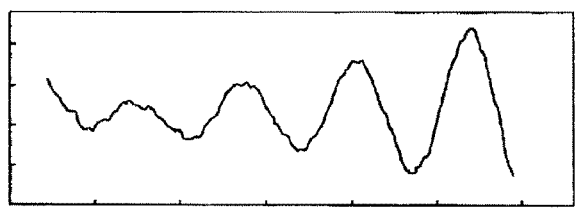
FIG. 20 is a graph showing a signal waveform of the characteristic value obtained under the conditions shown in FIG. 19.

FIG. 20 is a graph showing a signal waveform of the characteristic value obtained under the conditions shown in FIG. 19. As can be seen from FIG. 20, less noise appears on the signal waveform of the characteristic value, compared with the case of FIG. 18. If the moving average time is doubled, i.e., set to 10 seconds or if the rotational speed of the polishing table 112 is set to 70 min$^{-1}$ and the rotational speed of the top ring 114 is set to 84 min$^{-1}$, the sensor path makes substantially one revolution within the moving average time. Therefore, the accuracy of the polishing end point detection can be further improved.

Generally, when the moving average process is performed on time-series data, the processed data are obtained after a delay of about half the moving average time with respect to actual data. Further, if the ratio of the rotational speeds of the top ring 114 and the polishing table 112 is changed greatly, a distribution of the relative speed between the top ring 114 and the polishing table 112 on the substrate W varies and as a result a film-thickness profile of the substrate W is changed. Therefore, it is necessary to determine the moving average time, the rotational speed of the polishing table 112, and the rotational speed of the top ring 114 in consideration of permissible limits of a delay time depending on a CMP process and a degree of the change in the film-thickness profile. Generally, a slight change in the ratio of the rotational speeds of the top ring 114 and the polishing table 112 hardly affects the film-thickness profile. Therefore, it is easy to allow the sensor 150 to scan the surface of the substrate W substantially evenly only by adjustment of the ratio of the rotational speeds of the top ring 114 and the polishing table 112.

While the rotational speed of the top ring 114 is higher than the rotational speed of the polishing table 112 in the above-described example, the rotational speed of the top ring 114 may be lower than the rotational speed of the polishing table 112 (for example, the rotational speed of the polishing table 112 may be set to 70 min$^{-1}$ and the rotational speed of the top ring 114 may be set to 63 min$^{-1}$). In this case, the sensor path rotates in the opposite direction, but the paths of the sensor 150 described on the surface of the substrate W within the predetermined period of time are distributed over the entire circumference of the surface of the substrate W as well as the above example.

Further, while the ratio of the rotational speeds of the top ring 114 and the polishing table 112 is close to 1 in the above-described example, the ratio of the rotational speeds may be close to 0.5, 1.5, or 2 (i.e., a multiple of 0.5). In this case also, the same results can be obtained. For example, when the ratio of the rotational speeds of the top ring 114 and the polishing table 112 is set to 0.5, the sensor path rotates by 180 degrees each time the polishing table 112 makes one revolution. When viewed from the substrate W, the sensor 150 moves along the same path in the opposite direction each time the polishing table 112 makes one revolution.

The ratio of the rotational speeds of the top ring 114 and the polishing table 112 may be slightly shifted from 0.5 (for example, the rotational speed of the top ring 114 may be set to 36 $min^{-1}$ and the rotational speed of the polishing table 112 may be set to 70 $min^{-1}$), so that the sensor path rotates by 180+α degrees each time the polishing table 112 makes one revolution. In this case, the sensor path is shifted by an apparent angle of α degree(s). Therefore, it is possible to establish the value of α (i.e., the ratio of the rotational speeds of the top ring 114 and the polishing table 112) such that the sensor path rotates about 0.5 time, or about N time(s), or about 0.5+N times (in other words, a multiple of 0.5, i.e., 0.5×N time(s) (N is a natural number)) on the surface of the substrate W within the moving average time.

This method of distributing the paths of the sensor 150 on the surface of the substrate W substantially evenly over the circumference of the substrate W in its entirety within the moving average time can allow wide selection of the ratio of the rotational speeds, in consideration of the adjustment of the moving average time. Therefore, this method can be applied to a polishing process which requires great variation of the ratio of the rotational speeds of the top ring 114 and the polishing table 112 in accordance with polishing conditions such as characteristics of a polishing liquid (slurry).

Figure 21:
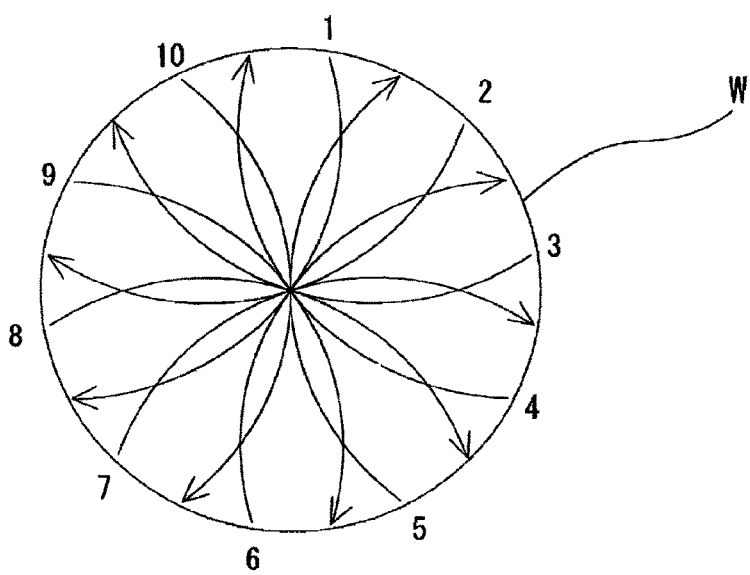
FIG. 21 is a view showing the sensor paths on the substrate while the polishing table makes ten revolutions under the same conditions as those in FIG. 19.

Generally, the path of the sensor 150 described on the substrate W is curved as shown in FIG. 19, except in a case where the rotational speed of the top ring 114 is just half the rotational speed of the polishing table 112. Therefore, even when the paths of the sensor 150 on the surface of the substrate W are distributed over the entire circumference of the substrate W within a predetermined time (e.g., the moving average time), these sensor paths are not evenly distributed in the circumferential direction of the substrate W in a strict sense. To exactly distribute the sensor paths evenly in the circumferential direction of the substrate W, it is necessary that the sensor path rotate just N time(s) (N is a natural number) on the substrate W in every predetermined period of time. During this period of time, the sensor 150 scans the surface of the substrate W in directions or orientations that are distributed evenly in the circumferential direction of the substrate W over the entire circumference thereof. To realize this, the rotational speeds of the polishing table 112 and the top ring 114 are determined such that, while the polishing table 112 makes a predetermined number (natural number) of revolutions, the top ring 114 makes just a predetermined number (natural number) of revolutions that is different from the predetermined number of revolutions of the polishing table 112. In this case also, since the sensor paths are curved as described above, it cannot be said that these paths are distributed at equal intervals in the circumferential direction. However, supposing that every two sensor paths make one pair, the sensor paths can be regarded as being distributed evenly in the circumferential direction at an arbitrary radial position. FIG. 21 shows this example. Specifically, FIG. 21 is a view showing the sensor paths on the substrate W while the polishing table 112 makes ten revolutions under the same conditions as those in FIG. 19. As can be understood from the above description, the sensor 150 can obtain data that more evenly reflect various structures of the entire surface of the substrate W, compared with the above example.

Next, a specific example according to the above-described principle will be described. In this example, a copper film is prepared as an object of polishing and an eddy current sensor is used as the sensor 150. A surface state of the substrate is monitored by the sensor 150, and real-time control for adjusting a distribution of pressing forces that press the substrate against the polishing surface is performed so as to provide a uniform film thickness with respect to the radial direction of the substrate. In the previously-described embodiment in which the optical sensor is used, all data obtained in one scanning operation can be averaged for use in processing operations. In this example, such an averaging process is not performed. Specifically, data indicating a film thickness, which are obtained while the sensor 150 scans the surface of the substrate W, are assigned to the zones C1, C2, C3, and C4 (see FIG. 15) distributed in the radial direction of the substrate W, and the data for the respective zones are used to determine the pressures in the pressure chambers corresponding to the respective zones. In this case, the moving average processing may be performed on the data, obtained as the polishing table 112 rotates, in each zone.

Figure 22:
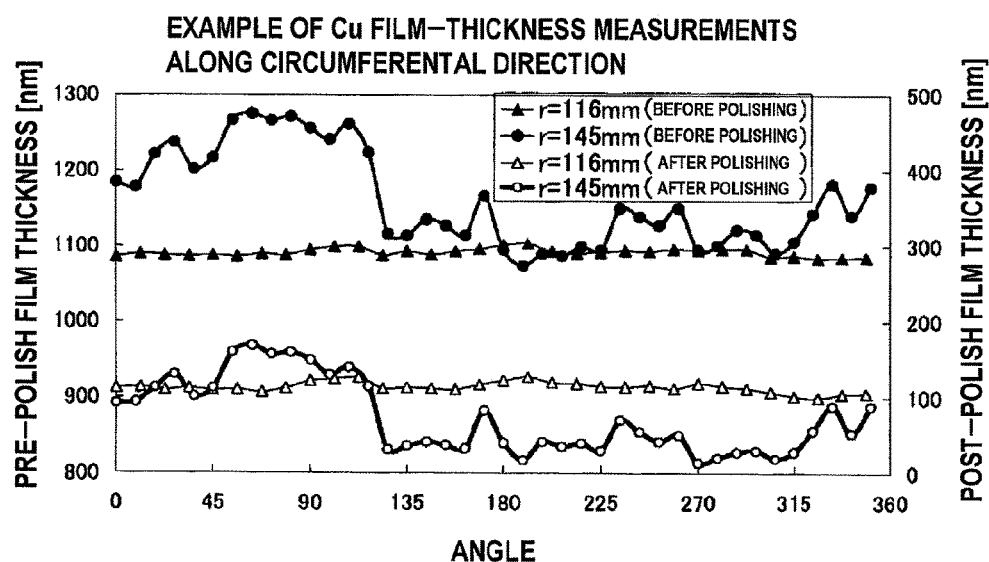
FIG. 22 is a graph showing an example of a pre-polish thickness and a post-polish thickness of a copper film, measured along a circumferential direction, formed on a substrate having a diameter of 300 mm.

FIG. 22 is a graph showing an example of a pre-polish thickness and a post-polish thickness of a copper film formed on a substrate having a diameter of 300 mm. In FIG. 22, the film thickness was measured along a circumferential direction of the substrate. As can be seen from FIG. 22, while the film thickness in the middle zone (a radius r=116 mm) is approximately uniform, considerable variations in the film thickness along the circumferential direction are observed in the peripheral zone (r=146 mm) of the substrate. This is because of the variations in contact resistance of the cathode electrodes (negative electrodes) arranged at equal intervals along the periphery of the substrate, or the variations in sealing performance of the seal member for retaining the plating solution. Possible causes of such variations in the contact resistance and the sealing performance include individual difference of parts, assembly error, and a secular change of parts. In addition, when using a plating apparatus having plural cells (plating baths) each for use in a plating process, the variations in the film thickness along the circumferential direction may differ depending on the cells. Moreover, the tendency of the variations in the film thickness can be changed by replacement of parts.

Figure 23:
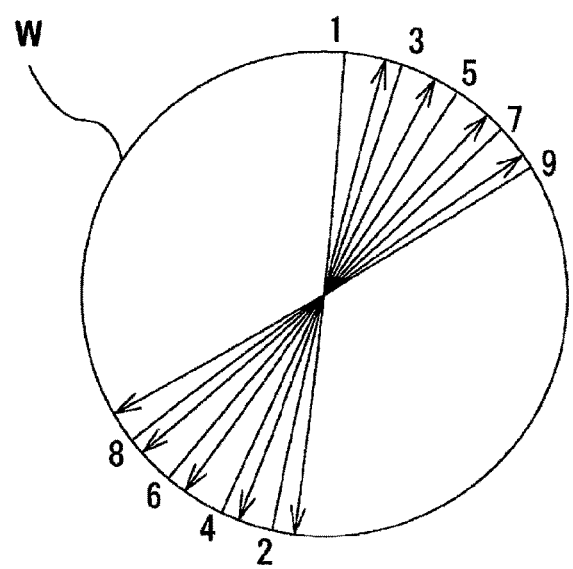
FIG. 23 is a view showing the sensor paths on the surface of the substrate when the rotational speed of the polishing table is set to 60 min$^{-1}$ and the rotational speed of the top ring is set to 31 min$^{-1}$.

FIG. 23 is a view showing the sensor paths on the surface of the substrate when the rotational speed of the polishing table 112 is set to 60 $min^{-1}$ and the rotational speed of the top ring 114 is set to 31 $min^{-1}$. In this example shown in FIG. 23, the sensor path rotates gradually, as well as the example shown in FIG. 17. The top ring 114 rotates through 186 degrees while the polishing table 112 makes one revolution (360-degree revolution). Therefore, when ignoring the scanning direction, the sensor path is returned to its original position after making half of one revolution around the surface of the substrate in 30 seconds. Therefore, if the moving average time is set to 5 seconds, the sensor scans only a thick-film portion or a thin-film portion in the periphery zone of the substrate W. This scanning operation may result in overestimation or underestimation of the film thickness.

Figure 24:
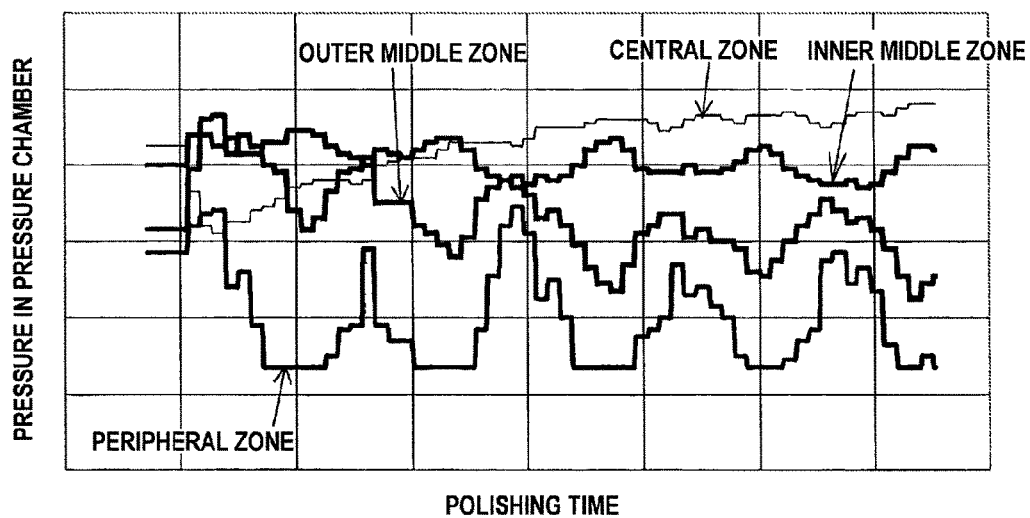
FIG. 24 is a graph showing results of an operation example in which pressures in four pressure chambers of the top ring are operated during polishing so as to make the film thickness uniform in zones C1, C2, C3, and C4 distributed along a radial direction of the substrate W.

FIG. 24 is a graph showing results of an operation example in which the pressures in the four pressure chambers (air bags) P1, P2, P3, and P4 of the top ring 114 are operated during polishing so as to make the film thickness uniform in the zones C1, C2, C3, and C4 distributed along the radial direction of the substrate W, under the above-described rotational speed conditions. As can be seen from FIG. 24, due to the influence of the variations in film thickness in the periphery of the substrate W along the circumferential direction, the pressure in outer pressure chamber fluctuates in a cycle of 30 seconds more greatly than the pressure in inner pressure chamber.

Figure 25:
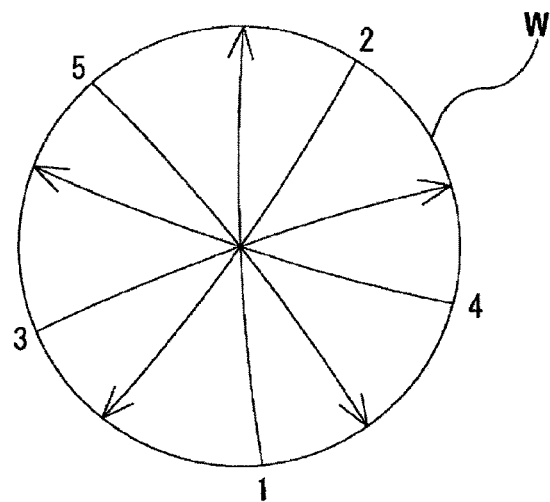
FIG. 25 is a view showing the sensor paths on the surface of the substrate when the rotational speed of the polishing table is adjusted to 60 min$^{-1}$ and the rotational speed of the top ring 114 is adjusted to 36 min$^{-1}$.

FIG. 25 is a view showing the sensor paths on the surface of the substrate when the rotational speed of the polishing table 112 is adjusted to 60 min$^{-1}$ and the rotational speed of the top ring 114 is adjusted to 36 min$^{-1}$ in order to avoid the above problem. In this example, as can be seen from FIG. 25, the sensor path makes substantially two revolutions in a counterclockwise direction each time the polishing table 112 makes five revolutions. During this period of time, the sensor 150 travels across the surface of the substrate W in directions or orientations that are distributed equally in the circumferential direction over the circumference of the substrate W in it entirety.

Figure 26:
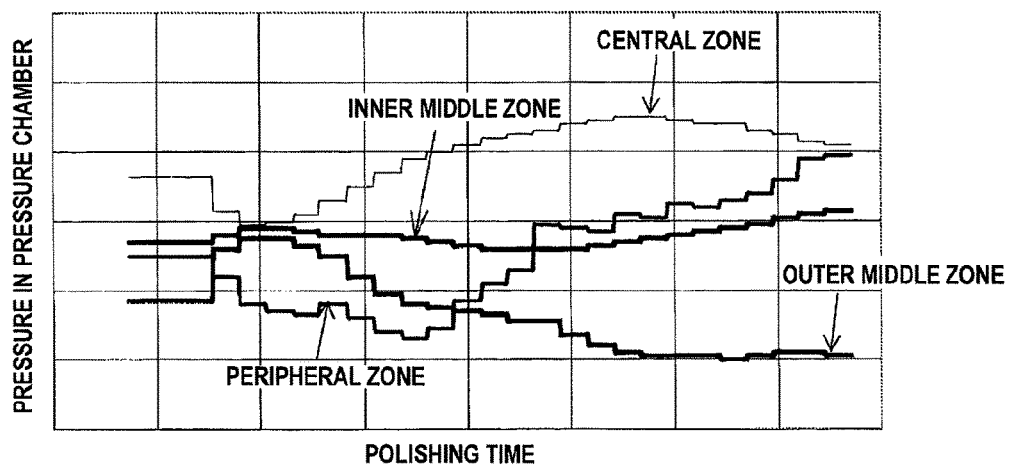
FIG. 26 is a graph showing changes in the pressures in the pressure chambers of the top ring when polishing the substrate under the conditions as shown in FIG. 25.

FIG. 26 is a graph showing changes in the pressures in the pressure chambers P1, P2, P3, and P4 of the top ring 114 when polishing the substrate under the conditions as shown in FIG. 25. In this example, the moving average time is set to 4 seconds. The moving average is performed on data of five points obtained at one-second intervals from a certain time back to a time by 4 seconds, i.e., data obtained while the polishing table 112 makes five revolutions. As shown in FIG. 26, the pressure fluctuation in a cycle of about 30 seconds as seen in FIG. 24 is not observed. Therefore, it is supposed that an average film thickness with respect to circumferential direction of the substrate is obtained by the sensor 150.

A relationship between the rotational speed of the polishing table 112 and the rotational speed of the top ring 114 for allowing the sensor 150 to scan the surface of the substrate W at equal angular intervals will now be described.

Where the sensor 150 sweeps across the surface of the substrate W in directions or orientations distributed evenly in the circumferential direction over the entire circumference of the substrate W while the polishing table 112 makes a predetermined number m (natural number) of revolutions, a relationship between a rotational speed V of the polishing table 112 and a rotational speed R of the top ring 114 is expressed by the following equation.

$$R/V = n/m \text{ that is, } m \cdot R/V = n \quad (9)$$

In this equation (9), R represents the rotational speed of the top ring;

V represents the rotational speed of the polishing table;

m represents the predetermined number of revolutions (m is a natural number) of the polishing table; and n represents the predetermined number of revolutions the top ring makes while the polishing table makes m revolution(s).

Where the sensor sweeps across the surface of the substrate W evenly such that the sensor path rotates around the entire circumference of the substrate W once while the polishing table makes m revolutions, m and n are relatively prime.

The principle as a basis of the above equation (9) is as follows. While the polishing table 112 makes m revolution(s), the top ring 114 makes m·R/V revolution(s). During this time, if the sensor 150 travels across the surface of the substrate W in directions or orientations distributed evenly in the circumferential direction over the entire circumference thereof, the top ring 114 is needed to make just n revolutions (see the equation (9)), provided that such situation does not occur before the polishing table 112 makes m revolutions (the top ring 114 makes n revolutions). In other words, m and n are natural numbers that are relatively prime.

From a different viewpoint of the equation (9), the relationship between the rotational speed V of the polishing table 112 and the rotational speed R of the top ring 114 can also be expressed by $$|(V-R)/V| \cdot m = n' \text{ that is, } |1-R/V| \cdot m = n' \quad (10)$$

where n' is a natural number and represents the number of revolutions the sensor path rotates on the surface of the substrate until the sensor path returns to its initial direction.

In this case, when V>R, $$m \cdot R/V = m-n', \text{ where } n' \text{ is } 1, 2, \ldots, m-1.$$

When V<R, $$m \cdot R/V = m+n', \text{ where } n' \text{ is } 1, 2, \ldots.$$

Therefore, if m−n' is replaced with n when V>R or m+n' is replaced with n when V<R, the equation (10) becomes equivalent to the equation (9). Specifically, the number of revolutions n' of the sensor path on the surface of the substrate is a difference between the number of revolutions m of the polishing table 112 and the number of revolutions n of the top ring 114.

In order to control the pressures in the pressure chambers P1, P2, P3, and P4 in real time in response to a change in film thickness during polishing, it is necessary to grasp a state of a film surface at a point of time as close to a point of time when determining the pressures as possible. For this reason, it is preferable that the value m be relatively small. For example, in order to grasp the surface state of the film within 16 seconds at the latest from a pressure determination time, the value m should be such that m/V≤16 seconds. On the other hand, in order to grasp an average surface state of the film without regard to the variations in film thickness in the circumferential direction and the difference in pattern density and structure, the value m is needed to be relatively large. In a case where the variations in film thickness in the circumferential direction are represented by eight measurements corresponding to at least four scan lines, m is not less than 4 (m≥4). Therefore, in view of the real-time control and the variations in film thickness, the number of revolutions m is preferably such that 4≤m≤16×V.

FIG. 27 is a table showing examples of a ratio R/V of the rotational speeds of the top ring and the polishing table which satisfies the equation (9). Actually, taking a polishing performance of the polishing apparatus into consideration, an appropriate ratio of the rotational speeds is selected from the table, so that the rotational speed of the top ring 114 and the rotational speed of the polishing table 112 are determined.

Due to some cause such as structures of the cell (i.e., the plating bath) of the plating apparatus, a spatial periodicity on a cycle of M may be observed in a change in film thickness at the periphery of the substrate. In such a case, the relationship between the rotational speed of the top ring 114 and the rotational speed of the polishing table 112 is expressed by the following equation.

$$R/V = n/(m \cdot M) \quad n=1,2,3,\ldots \quad (11)$$

If it is not until the polishing table 112 makes m revolutions that the scan line scans evenly the film thicknesses that vary along the circumferential direction of the substrate W, m and n are natural numbers that are relatively prime.

When the rotational speed of the polishing table 112 is set to an integral multiple of a setting unit (e.g., 1 min$^{-1}$) of the polishing apparatus based on the above equations (9), (10), and (11), the rotational speed of the top ring 114 may not be an integral multiple of the above-mentioned setting unit. In such a case, an integer close to a value determined from the above equations can be used for the rotational speed of the top ring 114. When the rotational speed of the polishing table 112 and the rotational speed of the top ring 114 are determined based on the above equations, the same portion of the polishing pad 16 polishes the same portion of the surface of the substrate W once, while the polishing table 112 makes m revolutions. This can cause a locally insufficient polishing of the substrate W due to the influence of the grooves on the polishing pad 16. In such a case, it is preferable to add or subtract a rotational speed which is the setting unit (e.g., 1 min$^{-1}$) of the polishing apparatus to or from the rotational speed of the polishing table 112 or the top ring 114.

For example, the rotational of the top ring 114 and the rotational speed of the polishing table 112 can be established in a range that is expressed by $$n \cdot V/m - 1 \leq R \leq n \cdot V/m + 1 \quad (12)$$

or $$m \cdot R/n - 1 \leq V \leq m \cdot R/n + 1 \quad (13)$$

where V is a rotational speed of the polishing table 112 and is a natural number indicating a multiple of the setting unit that is allowed by the polishing apparatus, and R is a rotational speed of the top ring 114 and is a natural number indicating a multiple of the setting unit that is allowed by the polishing apparatus.

Although the sensor 150 travels across the surface of the substrate W in the directions or orientations that are distributed evenly in the circumferential direction of the substrate W over its entire circumference, it is not necessary from a practical standpoint that the top ring 114 make just n revolutions while the polishing table 112 makes m revolutions. If an allowable range of revolution shift of the top ring 114 with respect to m revolutions of the polishing table 112 is ±0.2 revolution, the rotational speed of the polishing table 112 can be set within the following range.

$$m \cdot R/(n+0.2) \leq V \leq m \cdot R/(n-0.2) \quad (14)$$

The above-described method can be applied not only to the real-time control of the polishing process, but also to a process of detecting a polishing end point and a process of simply monitoring a film thickness. In the polishing control with the purpose of providing a uniform film thickness, a film thickness in the periphery of the substrate is regarded as important in most cases. However, in the polishing end point detection and the simple monitoring of the film thickness, it is not necessarily needed to monitor the periphery of the substrate, and a film thickness only in a central portion and/or its neighboring area may be monitored. In the central portion and its surrounding area, a surface state of substantially the same portion can be obtained even if the sensor path rotates through 180 degrees. Therefore, in the polishing end point detection and the simple monitoring of the film thickness, it is possible to replace n with n/2 in the above equation (9). In this case, the rotational speed ratio can be expressed by the following equation.

$$R/V = n/(2m) \quad (15)$$

In the above example, the moving average is used as a smoothing method for reducing noise components in the monitoring signal. However, any method can be used, as long as the method can substantially smooth the noise components generated in the monitoring signal in a cycle corresponding to the number of revolutions m. For example, an infinite impulse response digital filter may be used. Further, by appropriately setting a control cycle (specifically, a cycle of changing the pressures in the pressure chambers in response to the change in film thickness) so as not to synchronize with the number of revolutions m, good real-time control can be performed based on the monitoring signal without using the smoothing process (e.g., moving average).

As described above, the present invention can be applied to processing of the monitoring signal which indicates a polishing state outputted from an In-situ sensor, such as an optical or eddy current sensor, during planarization of a film formed on a surface of a substrate, such as a semiconductor wafer, by chemical mechanical polishing (CMP). The optical sensor is typically used in polishing of a silicon oxide film that allows light to pass therethrough. On the other hand, the eddy current sensor is used in polishing of a conductive film such as metal. However, the optical sensor can be used in polishing of a metal film with a thickness of less than several tens nm, because such a thin metal film allows light to pass therethrough.

The present invention can also be applied to a polishing process in which a film is polished using the monitoring signal so as to realize a uniform film thickness.

INDUSTRIAL APPLICABILITY

The present invention is applicable to processing end point detection method and apparatus for detecting a timing of a processing end point by calculating a characteristic value of a surface of a workpiece (an object of polishing) such as a substrate.

The invention claimed is:
1. A polishing method, comprising:
holding and rotating a workpiece by a top ring;
pressing the workpiece against a polishing surface on a rotating polishing table to polish the workpiece; and
monitoring a surface state of the workpiece by measuring a film thickness of the workpiece with a sensor provided on the polishing table during polishing of the workpiece, the sensor being either an optical sensor or an eddy current sensor,
wherein a rotational speed of the top ring and a rotational speed of the polishing table are set such that, while the polishing table makes a predetermined number of revolutions which is expressed by a first natural number, the top ring makes a predetermined number of revolutions which is expressed by a second natural number,
the first natural number and the second natural number are relatively prime, and
the first natural number is not less than 4 and not more than a number of revolutions the polishing table makes within 16 seconds.
2. The polishing method according to claim 1, further comprising:
detecting a polishing end point by said monitoring of the surface state of the workpiece by the sensor.
3. The polishing method according to claim 1, further comprising:
during said monitoring of the surface state of the workpiece by the sensor, polishing the workpiece so as to provide a uniform film thickness of the surface of the workpiece.
4. A polishing method comprising:
holding and rotating a workpiece by a top ring;
pressing the workpiece against a polishing surface on a rotating polishing table to polish the workpiece; and
monitoring a surface state of the workpiece by measuring a film thickness of the workpiece with a sensor pro- vided on the polishing table during polishing of the workpiece, the sensor being either an optical sensor or an eddy current sensor, wherein a rotational speed of the top ring and a rotational speed of the polishing table satisfy a relational expression given by $$n \cdot V/m - 1 \leq R \leq n \cdot V/m + 1 \text{ or } m \cdot R/n - 1 \leq V \leq m \cdot R/n + 1$$

where V is the rotational speed of the polishing table and is a natural number indicating a multiple of a setting unit that is allowed by a polishing apparatus, R is the rotational speed of the top ring and is a natural number indicating a multiple of the setting unit that is allowed by the polishing apparatus, m is a predetermined natural number that indicates the number of revolutions the polishing table makes while the sensor travels across the surface of the workpiece in directions or orientations distributed evenly in a circumferential direction of the workpiece over an entire circumference thereof, and n is a natural number such that m and n are relatively prime.

5. The polishing method according to claim 4, further comprising:

detecting a polishing end point by said monitoring of the surface state of the workpiece by the sensor.

6. The polishing method according to claim 4, wherein during said monitoring of the surface state of the workpiece by the sensor, polishing of the workpiece is performed so as to provide a uniform film thickness of the surface of the workpiece.

7. A polishing apparatus comprising:

a top ring configured to hold and rotate a workpiece;

a rotatable polishing table having a polishing surface, said top ring being configured to press the workpiece against the polishing surface; and a sensor provided on said polishing table and configured to monitor a surface state of the workpiece by measuring a film thickness of the workpiece during polishing of the workpiece, said sensor being either an optical sensor or an eddy current sensor, wherein a rotational speed of said top ring and a rotational speed of said polishing table are set such that, while said polishing table makes a predetermined number of revolutions which is expressed by a first natural number, said top ring makes a predetermined number of revolutions which is expressed by a second natural number, the first natural number and the second natural number are relatively prime, and the first natural number is not less than 4 and not more than a number of revolutions said polishing table makes within 16 seconds.

8. The polishing apparatus according to claim 7, further comprising:

an end point detector configured to detect a polishing end point based on the surface state of the workpiece obtained by said sensor.

9. The polishing apparatus according to claim 7, further comprising:

a controller configured to determine forces of pressing the workpiece against the polishing surface so as to uniformly polish the surface of the workpiece, based on the surface state of the workpiece obtained by said sensor.

10. A polishing apparatus comprising:

a top ring configured to hold and rotate a workpiece;

a rotatable polishing table having a polishing surface, said top ring being configured to press the workpiece against the polishing surface; and a sensor provided on said polishing table and configured to monitor a surface state of the workpiece by measuring a film thickness of the workpiece during polishing of the workpiece, said sensor being either an optical sensor or an eddy current sensor, wherein a rotational speed of said top ring and a rotational speed of said polishing table satisfy a relational expression given by $$n \cdot V/m - 1 \leq R \leq n \cdot V/m + 1 \text{ or } m \cdot R/n - 1 \leq V \leq m \cdot R/n + 1$$

where V is the rotational speed of said polishing table and is a natural number indicating a multiple of a setting unit that is allowed by a polishing apparatus, R is the rotational speed of said top ring and is a natural number indicating a multiple of the setting unit that is allowed by the polishing apparatus, m is a predetermined natural number that indicates the number of revolutions said polishing table makes while said sensor travels across the surface of the workpiece in directions or orientations distributed evenly in a circumferential direction of the workpiece over an entire circumference thereof, and n is a natural number such that m and n are relatively prime.

11. The polishing apparatus according to claim 10, further comprising:

an end point detector configured to detect a polishing end point based on the surface state of the workpiece obtained by said sensor.

12. The polishing apparatus according to claim 10, further comprising:

a controller configured to determine forces of pressing the workpiece against the polishing surface so as to uniformly polish the surface of the workpiece, based on the surface state of the workpiece obtained by said sensor.

* * * * *

UNITED STATES PATENT AND TRADEMARK OFFICE
CERTIFICATE OF CORRECTION

PATENT NO. : 10,207,390 B2  
APPLICATION NO. : 14/017620  
DATED : February 19, 2019  
INVENTOR(S) : Noburu Shimizu et al.

Page 1 of 1

It is certified that error appears in the above-identified patent and that said Letters Patent is hereby corrected as shown below:

On the Title Page

In Item (73) Assignee, please change "TOSHIBA MEMORY CORPORATION, Tokyo (JP)" to -- EBARA CORPORATION, Tokyo (JP) and TOSHIBA MEMORY CORPORATION, Tokyo (JP) --.

Signed and Sealed this  
Twenty-sixth Day of November, 2019

Andrei Iancu  
*Director of the United States Patent and Trademark Office*